(12) United States Patent
Yajima

(10) Patent No.: US 12,114,942 B2
(45) Date of Patent: Oct. 15, 2024

(54) INFORMATION PROCESSING APPARATUS, INFORMATION PROCESSING SYSTEM, AND INFORMATION PROCESSING METHOD

(71) Applicant: SONY GROUP CORPORATION, Tokyo (JP)

(72) Inventor: Shunsuke Yajima, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 185 days.

(21) Appl. No.: 17/753,789

(22) PCT Filed: Sep. 16, 2020

(86) PCT No.: PCT/JP2020/035066
§ 371 (c)(1),
(2) Date: Mar. 15, 2022

(87) PCT Pub. No.: WO2021/060104
PCT Pub. Date: Apr. 1, 2021

(65) Prior Publication Data
US 2022/0378525 A1 Dec. 1, 2022

(30) Foreign Application Priority Data
Sep. 24, 2019 (JP) .................................. 2019-173587

(51) Int. Cl.
*G06F 17/00* (2019.01)
*A61B 34/30* (2016.01)
(Continued)

(52) U.S. Cl.
CPC ................. *A61B 34/30* (2016.02); *B25J 3/00* (2013.01); *B25J 13/085* (2013.01); *B25J 13/089* (2013.01); *G06N 20/20* (2019.01)

(58) Field of Classification Search
CPC ... A61B 34/30; A61B 2090/064; A61B 34/37; B25J 3/00; B25J 13/085; B25J 13/089;
(Continued)

(56) References Cited

U.S. PATENT DOCUMENTS 11,273,069 B2 * 3/2022 Agrawal ............. A61F 5/05883
11,285,603 B2 * 3/2022 Yamada ................. B25J 9/1669
(Continued)

FOREIGN PATENT DOCUMENTS

CN 107962558 A 4/2018
CN 109129462 A 1/2019
(Continued)

OTHER PUBLICATIONS

End-Efector Force and Joint Torque Esimation of a 7-DoF Robotic Manipulator Using Deep Learning (Year: 2021).*
(Continued)

*Primary Examiner* — Ronnie M Mancho
(74) *Attorney, Agent, or Firm* — CHIP LAW GROUP

(57) ABSTRACT

An information processing apparatus (100) includes an estimation unit (133) configured to estimate an external force estimation value which is an estimation value for an external force that acts on an object to be driven by performing a process based on a machine learning model with a force estimation value and an external force response value as an input, the force estimation value being an estimation value for a force that acts on the object to be driven, the external force response value being based on a value of an external force detected by a force sensor configured to detect the external force that acts on the object to be driven.

15 Claims, 13 Drawing Sheets

(51) Int. Cl.
  *B25J 3/00*    (2006.01)
  *B25J 13/08*   (2006.01)
  *G06N 20/20*   (2019.01)

(58) Field of Classification Search
  CPC ..... B25J 3/04; B25J 9/163; B25J 9/161; B25J 9/1689; G06N 20/20; G06N 3/0442; G06N 3/0475; G06N 3/08
  USPC .......................................................... 700/258
  See application file for complete search history.

(56) References Cited

U.S. PATENT DOCUMENTS

| | | | |
|---|---|---|---|
| 11,471,232 B2* | 10/2022 | Bowling | B25J 9/1633 |
| 11,559,894 B2* | 1/2023 | Oka | B25J 9/161 |
| 11,648,681 B2* | 5/2023 | Ju | B25J 9/1607 |
| | | | 700/245 |
| 11,672,491 B2* | 6/2023 | Fishman | A61B 6/4458 |
| | | | 600/3 |
| 11,672,620 B2* | 6/2023 | Bowling | B25J 9/1633 |
| | | | 700/261 |
| 11,850,751 B2* | 12/2023 | Matsuda | B25J 9/1633 |
| 2018/0107174 A1 | 4/2018 | Takahashi | |
| 2018/0361576 A1 | 12/2018 | Sakai | |
| 2021/0323148 A1* | 10/2021 | Matsuda | B25J 9/1633 |
| 2021/0394362 A1* | 12/2021 | Sodeyama | B25J 9/163 |
| 2021/0402596 A1* | 12/2021 | Karito | B25J 9/1633 |
| 2022/0003620 A1* | 1/2022 | Shafer | B25J 13/085 |
| 2022/0168047 A1* | 6/2022 | Nagao | A61B 1/0016 |
| 2022/0221364 A1* | 7/2022 | Zhou | G01L 5/16 |
| 2022/0378525 A1* | 12/2022 | Yajima | B25J 3/04 |
| 2022/0402708 A1* | 12/2022 | Pidaparthi | B25J 9/1697 |
| 2022/0405439 A1* | 12/2022 | Pidaparthi | G06F 30/20 |
| 2023/0006590 A1* | 1/2023 | Shimamoto | H02P 23/14 |
| 2023/0110897 A1* | 4/2023 | Kansky | B25J 9/1664 |
| | | | 700/253 |

FOREIGN PATENT DOCUMENTS

| | | |
|---|---|---|
| DE | 102017009471 A1 | 4/2018 |
| DE | 102018113656 A1 | 12/2018 |
| JP | 07-319558 A | 12/1995 |
| JP | 2018-065221 A | 4/2018 |
| JP | 2018-202504 A | 12/2018 |
| JP | 2019-000942 A | 1/2019 |
| JP | 2019-130602 A | 8/2019 |
| WO | 2018/221035 A1 | 12/2018 |
| WO | 2019/150866 A1 | 8/2019 |

OTHER PUBLICATIONS

International Search Report and Written Opinion of PCT Application No. PCT/JP2020/035066, dated Nov. 2, 2020, 08 pages of ISRWO.

* cited by examiner

INFORMATION PROCESSING APPARATUS, INFORMATION PROCESSING SYSTEM, AND INFORMATION PROCESSING METHOD

CROSS REFERENCE TO RELATED APPLICATIONS

This application is a U.S. National Phase of International Patent Application No. PCT/JP2020/035066 filed on Sep. 16, 2020, which claims priority benefit of Japanese Patent Application No. JP 2019-173587 filed in the Japan Patent Office on Sep. 24, 2019. Each of the above-referenced applications is hereby incorporated herein by reference in its entirety.

FIELD

The present invention relates to an information processing apparatus, an information processing system, and an information processing method.

BACKGROUND

According to the prior art, a technique for controlling the operation of a robot is known. For example, a technique of classifying a force detected by a robot into an external force, an internal force, and noise by machine learning has been proposed.

CITATION LIST

Patent Literature

Patent Literature 1: JP 2018-65221 A

SUMMARY

Technical Problem

However, in the above-described prior art, it is not always possible to appropriately control the operation of the robot. For example, in the above-described prior art, a force applied to the robot is detected by a force sensor or the like, and the force detected by the force sensor or the like is merely classified into an external force, an internal force, and noise by machine learning, and it is not always possible to appropriately control the operation of the robot.

Therefore, an object of the present disclosure is to provide an information processing apparatus, an information processing system, and an information processing method capable of appropriately controlling the operation of a robot.

Solution to Problem

To solve the above problem, an information processing apparatus comprising:

an estimation unit configured to estimate an external force estimation value which is an estimation value for an external force that acts on an object to be driven by performing a process based on a machine learning model with a force estimation value and an external force response value as an input, the force estimation value being an estimation value for a force that acts on the object to be driven, the external force response value being based on a value of an external force detected by a force sensor configured to detect the external force that acts on the object to be driven.

DESCRIPTION OF EMBODIMENTS

Figure 1:
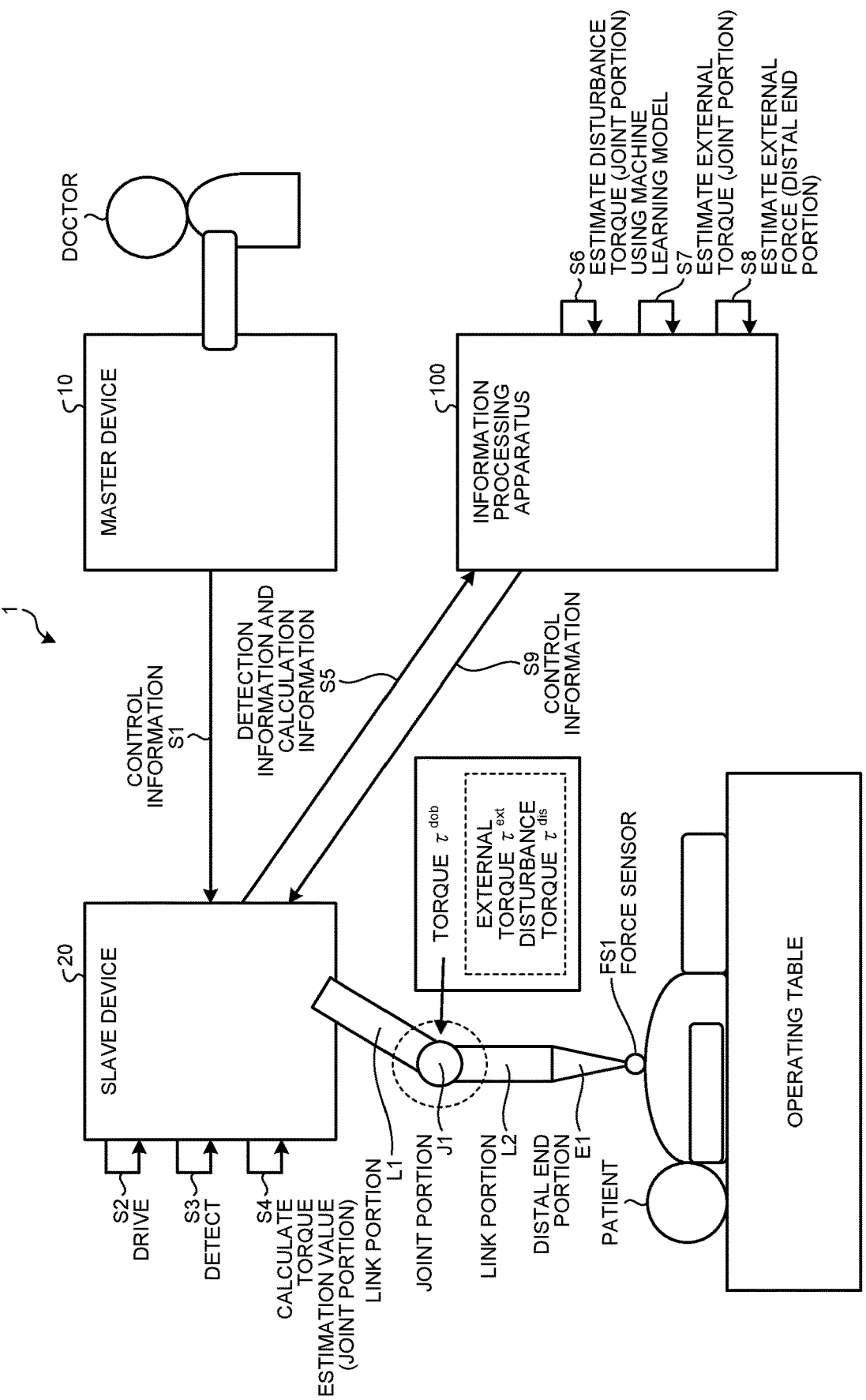
FIG. 1 is a diagram illustrating an example of information processing according to an embodiment of the present disclosure.

Hereinafter, embodiments of the present disclosure will be described in detail with reference to the drawings. In each of the following embodiments, the same parts are denoted by the same reference numerals, and redundant description will be omitted.

The present disclosure will be described according to the following order of items.

1. Embodiment
 1-1. Overview of Information Processing According to Embodiment
 1-2. Configuration of Information Processing System According to Embodiment 1-3. Process of Information Processing According to Embodiment
1-4. Configuration of Master Device According to Embodiment
1-5. Configuration of Slave Device According to Embodiment
1-6. Configuration of Information Processing Apparatus According to Embodiment
1-6-1. Configuration of Control Unit According to Embodiment
1-7. Details of Information Processing According to Embodiment
1-7-1. Example of Learning Processing According to Embodiment
1-7-2. Configuration Example of Machine Learning Model
1-7-3. Example of Learning Data
1-7-4. Example of Estimation Processing According to Embodiment
1-7-5. Estimation Accuracy of Machine Learning Model
1-8. Procedure of Information Processing According to Embodiment
1-8-1. Procedure of Learning Processing According to Embodiment
1-8-2. Procedure of Estimation Processing According to Embodiment
1-9. Modification of Embodiment
1-9-1. First Modification of Embodiment
1-9-2. Second Modification of Embodiment
2. Other Embodiments
2-1. Case Where External Force Due to Contact Outside Force Sensor Acts
2-2. Application to Industrial Robot
2-3. Application to Linear Motion Joint
3. Effects According to Present Disclosure
4. Hardware Configuration 1. Embodiment 1-1. Overview of Information Processing According to Embodiment First, an overview of information processing according to an embodiment of the present disclosure will be described with reference to FIG. 1. FIG. 1 is a diagram illustrating an example of information processing according to the embodiment of the present disclosure. The information processing according to the embodiment of the present disclosure is implemented by an information processing system 1 illustrated in FIG. 1. As illustrated in FIG. 1, the information processing system 1 according to the embodiment of the present disclosure is a master-slave information processing system including a master device 10 operated by an operator (doctor in FIG. 1) and a slave device 20 remotely controlled from the master device 10 in accordance with an operation by the operator.

In the information processing system 1 illustrated in FIG. 1, the slave device 20 located on the patient side includes an arm portion corresponding to an arm. The arm portion grips a medical instrument for performing a medical practice on a patient. The master device 10 receives an input of operation information of the arm portion by the operator. The slave device 20 receives the operation information of the arm portion from the master device 10 and operates the arm portion.

Furthermore, the information processing system 1 according to the embodiment of the present disclosure employs bilateral control as an example. The bilateral control is feedback control in which the position (displacement) and the force are matched between the master device 10 and the slave device 20. For example, when the master device 10 receives an input of operation information to the arm portion by the operator, the slave device 20 moves the position of the arm portion in accordance with the operation information. When the slave device 20 moves the position of the arm portion and comes into contact with the patient, the slave device 20 feeds back the force generated by the contact between the patient and the arm portion to the operator of the master device 10.

1-2. Configuration of Information Processing System According to Embodiment

Figure 2:
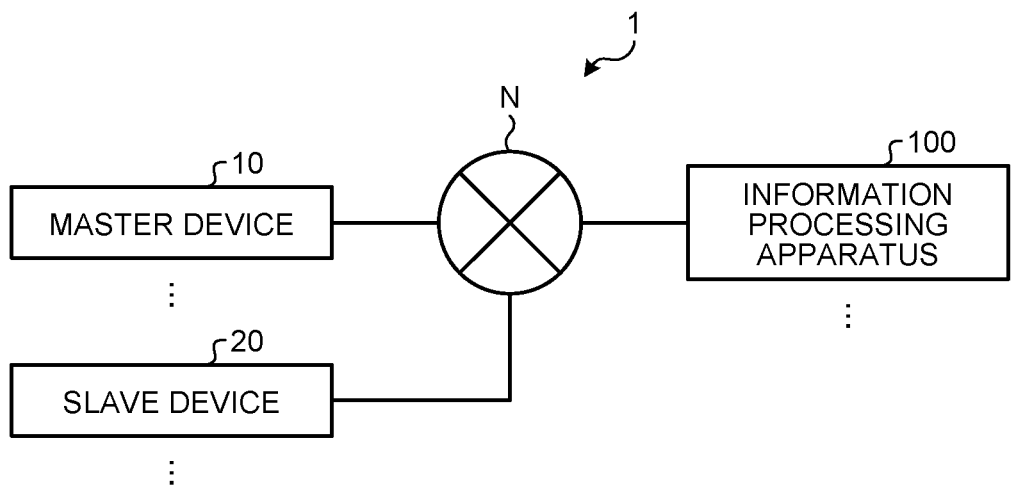
FIG. 2 is a diagram illustrating a configuration example of an information processing system according to the embodiment of the present disclosure.

Next, a configuration of the information processing system according to the embodiment of the present disclosure will be described with reference to FIGS. 1 and 2. FIG. 2 is a diagram illustrating a configuration example of the information processing system according to the embodiment of the present disclosure. As illustrated in FIG. 2, the information processing system 1 includes the master device 10, the slave device 20, and an information processing apparatus 100. The master device 10, the slave device 20, and the information processing apparatus 100 are connected to be able to communicate in a wired or wireless manner via a predetermined network N. Note that the information processing system 1 illustrated in FIG. 2 may include an arbitrary number of master devices 10, an arbitrary number of slave devices 20, and an arbitrary number of information processing apparatus 100.

The master device 10 is a robot apparatus used to operate the slave device 20 in accordance with the operation by the operator. The master device 10 is a robot apparatus including a master arm or the like for the operator to remotely operate the slave device 20.

The slave device 20 is a robot apparatus that operates the arm portion that grips a medical instrument in accordance with an operation input from the master device 10. For example, the slave device 20 is a manipulator (robot apparatus having a link mechanism including an active joint) having one or two or more active joints for moving in accordance with the operation content received from the operator and a link connected to the active joint. Note that the active joint is a joint moved by driving of a motor. Hereinafter, the active joint is simply referred to as the joint. In addition, a portion of the robot apparatus corresponding to a joint will be referred to as a joint portion. Further, a portion of the robot apparatus corresponding to the link will be referred to as a link portion. Furthermore, a portion of the robot apparatus including a joint portion and a plurality of link portions connected by the joint portion will be referred to as the arm portion.

In general, the motion of the arm structure in which the plurality of link portions are connected to each other by the joint portion can be expressed by the following mathematical expression (1). Here, x is a vector including coordinates indicating the position of the distal end of each link portion constituting the arm structure, and θ is a vector indicating a rotation angle in each joint portion (a rotation angle of another link portion with respect to one link portion connected by the joint portion). In addition, $J_{aco}$ is a Jacobian matrix (Jacobian) with respect to θ of x.

$$\dot{x}(\theta) = J_{aco}(\theta)\dot{\theta} \quad (1)$$

The slave device 20 according to the embodiment of the present disclosure includes a motor, a joint portion that rotates by driving of the motor, a force sensor that detects an external force acting on an arm portion with the joint portion, and a calculator that calculates a torque estimation value that is an estimation value of a torque acting on the joint portion. In an example illustrated in FIG. 1, the slave device 20 includes an arm portion including a link portion L1, a joint portion J1 that rotates by driving of a motor, a link portion L2 connected to the link portion L1 by the joint portion J1, and a distal end portion E1 coupled to the link portion L2, and a force sensor FS1 that detects an external force acting on the arm portion. Although not illustrated in FIG. 1, the slave device 20 includes a disturbance observer (DOB) that is a calculator for calculating a torque estimation value that is an estimation value of the torque acting on the joint portion J1. Note that the joint portion J1 of the arm portion has a function of an actuator including a motor, a speed reducer, and an encoder.

Note that, in practice, the arm portion of the slave device 20 includes a plurality of joint portions Ji (i=1, 2, ...) (not illustrated). In FIG. 1, one joint portion J1 of a plurality of joint portions Ji (i=1, 2, ...) will be described as an example for the sake of better understanding.

Upon receiving the control information from the master device 10, the slave device 20 controls the rotational motion of the joint portion J1 by driving the motor. More specifically, the slave device 20 controls the number of rotation of the motor by controlling the amount of current supplied to the motor in the actuator of the joint portion J1, and controls the rotation angle and the generated torque in the joint portion J1. The slave device 20 controls the operation of the arm portion as the joint portion J1 controls the rotational motion.

In addition, the slave device 20 detects the current value input to the motor of the joint portion J1 and the power value related to the output of the motor by the disturbance observer. The disturbance observer calculates a torque estimation value that is an estimation value of the torque acting on the joint portion J1 on the basis of the current value input to the motor and the power value related to the output of the motor.

In addition, a medical instrument that comes into contact with the patient is provided at the distal end portion E1 which is a distal end portion of the arm portion. In addition, the force sensor FS1 is provided at the distal end portion E1. The force sensor FS1 detects a force generated by contact between the patient and the medical instrument. More specifically, the force sensor FS1 detects a reaction force (external force) acting on the distal end portion E1 of the arm portion by the contact between the patient and the medical instrument.

The information processing apparatus 100 is an information processing apparatus that estimates an external force estimation value that is a value of an estimated external force estimated to act on the arm portion. In general, in a master slave system, it is preferable to detect an external force generated due to contact between a patient and a medical instrument with high sensitivity and present a doctor with an operation feeling similar to actual contact between the patient and the medical instrument. For this purpose, it is desirable to present the doctor with an operation feeling in a state in which a force other than the external force generated due to the contact between the patient and the medical instrument, for example, the influence of disturbance acting on the arm device is removed as much as possible.

Specifically, disturbance due to frictional force, gravity, centrifugal force, Coriolis force, and modeling error acts on the joint portion J1 of the arm portion. Then, when a disturbance acts on the joint portion J1 of the arm portion, the rotational motion of the joint portion J1 is hindered as compared with an ideal joint portion which neglects the influence of the disturbance. For example, when the frictional force acts on the joint portion J1 of the arm portion, the joint portion J1 does not rotate smoothly as compared with the case of an ideal joint portion which neglects the influence of the frictional force. Furthermore, when the joint portion J1 does not rotate smoothly, the movement of the arm portion is hindered in conjunction therewith. As a result, for example, the external force estimation value estimated to act on the distal end portion E1 of the arm portion deviates from the ideal value as compared with the ideal joint portion which neglects the influence of the frictional force. That is, when the frictional force acts on the joint portion J1 of the arm portion, an operation feeling similar to actual contact between the patient and the medical instrument is hindered. For example, there is a possibility that an unpreferable operation feeling such as slow movement of the arm portion (alternatively, the arm portion is heavy.) is transmitted to a doctor operating the arm portion of the slave device 20 via the master device 10.

In this manner, in general, when a disturbance acts on the joint portion J1 of the arm portion, the motion state of the joint portion changes as compared with an ideal joint portion which neglects the influence of the disturbance. In addition, when the motion state of the joint portion changes, the motion state of the arm portion changes in conjunction with the change. As a result, for example, the external force estimation value estimated to act on the distal end portion E1 of the arm portion changes as compared with the ideal joint portion which neglects the influence of disturbance. That is, operation feeling similar to actual contact between the patient and the medical instrument is disturbed. For example, there is a possibility that the operating feeling as being operating with the robot is transmitted to the doctor who is operating the arm portion of the slave device 20 via the master device 10. Then, such an operation feeling as being operating with the robot may adversely affect the operation of the master device by the doctor. Therefore, it is necessary to remove the influence of the disturbance acting on the joint portion J1 of the arm portion as much as possible. Note that, as described above, since the actual arm portion includes the plurality of joint portions Ji (i= 1, 2, ...), it is necessary to remove the influence of disturbance acting on each joint portion Ji of the arm portion as much as possible.

Therefore, the slave device 20 according to the embodiment of the present disclosure calculates, using the disturbance observer, the torque estimation value $\tau^{dob}$ ($\tau^{dob}$ added with a caret) that is the estimation value of the torque estimated to have acted on each joint portion Ji of the arm portion on the basis of the current value input to the motor of each joint portion Ji (i=1, 2, ...) and the power value related to the output of the motor. In addition, the slave device 20 detects, using the force sensor FS1, the external force acting on the distal end portion E1 of the arm portion.

The information processing apparatus 100 according to the embodiment of the present disclosure acquires, from the slave device 20, the torque estimation value $\tau^{dob}$ ($\tau^{dob}$ added with a caret) calculated by the disturbance observer and a response value $f^{ext}$ of the external force detected by the force sensor FS1.

Here, the torque calculated as the torque acting on each joint portion Ji of the arm portion in accordance with the external force acting on the distal end portion E1 of the arm portion is referred to as an external torque response value $\tau^{ext}$. Then, the external torque response value $\tau^{ext}$ is calculated as in the following mathematical expression (2) using the transposed matrix $J^T_{aco}$ of the Jacobian matrix $J_{aco}$ and the response value $f^{ext}$ of the external force detected by the force sensor FS1.

$$\tau^{ext} = J_{aco}{}^T f^{ext} \qquad (2)$$

When acquiring the response value $f^{ext}$ of the external force detected by the force sensor FS1, the information processing apparatus 100 calculates the external torque response value $\tau^{ext}$ of each of the joint portions Ji using the above mathematical expression (2).

In a case where the torque estimation value $\tau^{dob}$ ($\tau^{dob}$ added with a caret) of each joint portion Ji and the external torque response value $\tau^{ext}$ of each joint portion Ji are input as inputs of a machine learning model M1, the information processing apparatus 100 causes the machine learning model M1 to learn so that a disturbance torque estimation value $\tau^{dib}$ ($\tau^{dib}$ added with a caret) of each joint portion Ji calculated using the following mathematical expression (3) is output as an output of the machine learning model M1.

$$\hat{\tau}^{dis} = \hat{\tau}^{dob} - \tau^{ext} \qquad (3)$$

In addition, the information processing apparatus 100 estimates the disturbance torque estimation value $\tau^{dib}$ ($\tau^{dib}$ added with a caret) acting on each joint portion Ji on the basis of the torque estimation value $\tau^{dob}$ ($\tau^{dob}$ added with a caret) of each joint portion Ji and the external torque response value $\tau^{ext}$ acting on each joint portion Ji using the learned machine learning model M1.

After estimating the disturbance torque estimation value $\tau^{dib}$ ($\tau^{dib}$ added with a caret) using the machine learning model M1, the information processing apparatus 100 calculates the external torque estimation value $\tau^{ext}$ ($\tau^{ext}$ added with a caret), which is an estimation value of the torque estimated to have acted on each joint portion Ji, using the following mathematical expression (4). Specifically, the information processing apparatus 100 calculates the external torque estimation value $\tau^{ext}$ ($\tau^{ext}$ added with a caret) of each joint portion Ji by subtracting the disturbance torque estimation value $\tau^{dib}$ ($\tau^{dib}$ added with a caret) estimated using the machine learning model M1 from the torque estimation value $\tau^{dob}$ ($\tau^{dob}$ added with a caret) of each joint portion Ji.

$$\hat{\tau}^{ext} = \hat{\tau}^{dob} - \hat{\tau}^{dis} \qquad (4)$$

Furthermore, the information processing apparatus 100 coordinate-transforms the external torque estimation value $\tau^{ext}$ ($\tau^{ext}$ added with a caret) of each joint portion Ji from the joint space to the operation space of the arm portion, thereby calculating the external force estimation value $f^{ext}$ ($f^{ext}$ added with a caret) estimated to have acted on the distal end portion E1 of the arm portion. Specifically, the external force estimation value $f^{ext}$ ($f^{ext}$ added with a caret) is calculated as in the following mathematical expression (5) using the inverse transposed matrix $J^{-T}_{aco}$ of the Jacobian matrix $J_{aco}$ and the external torque estimation value $\tau^{ext}$ ($\tau^{ext}$ added with a caret) of each joint portion Ji.

$$\hat{f}^{ext} = J_{aco}{}^{-T} \hat{\tau}^{ext} \qquad (5)$$

The information processing apparatus 100 according to the embodiment of the present disclosure uses the machine learning model M1 learned to estimate the disturbance torque estimation value $\tau^{dib}$ ($\tau^{dib}$ added with a caret) of each joint portion Ji on the basis of the torque estimation value $\tau^{dob}$ ($\tau^{dob}$ added with a caret) of each joint portion Ji and the external torque response value $\tau^{ext}$ acting on each joint portion Ji, thereby being able to estimate the disturbance torque estimation value $\tau^{dib}$ ($\tau^{dib}$ added with a caret) acting on each joint portion Ji with higher accuracy than in the prior art. As a result, the information processing apparatus 100 can estimate the external torque estimation value $\tau^{ext}$ ($\tau^{ext}$ added with a caret) estimated to act on each joint portion Ji of the arm portion with higher accuracy using the above mathematical expression (4). Therefore, the information processing apparatus 100 can estimate the external force estimation value $f^{ext}$ ($f^{ext}$ added with a caret) estimated to act on the distal end portion E1 of the arm portion with higher accuracy using the above mathematical expression (5).

1-3. Process of Information Processing According to Embodiment

Here, a process of information processing according to the embodiment of the present disclosure will be described with reference to FIG. 1. Note that, although the arm portion of the slave device 20 actually includes a plurality of joint portions Ji (i=1, 2, . . . ) (not illustrated), for the sake of better understanding, in FIG. 1, one joint portion J1 of the plurality of joint portions Ji (i=1, 2, . . . ) will be described as an example.

In FIG. 1, the master device 10 receives an operation input to the arm portion of the slave device 20 by a doctor. The master device 10 converts the operation content received from the operator into control information for controlling driving on the slave device 20 side. The master device 10 transmits the converted control information to the slave device 20 (Step S1).

The slave device 20 receives control information corresponding to the operation content received from the operator from the master device 10. The slave device 20 moves the arm portion according to the control information received from the master device 10. Specifically, the slave device 20 drives the motor in accordance with the control information (Step S2). More specifically, the slave device 20 controls the number of rotation of the motor by controlling the amount of current supplied to the motor in the actuator of the joint portion J1, and controls the rotation angle and the generated torque in the joint portion J1. The slave device 20 controls the operation of the arm portion by controlling the rotational motion of the joint portion J1. For example, the slave device 20 moves the arm portion to a position in contact with the patient in accordance with the control information.

When the slave device 20 moves the arm portion and the distal end portion E1 of the arm portion comes into contact with the patient, the force sensor FS1 provided at the distal end portion E1 of the arm portion detects an external force acting on the distal end portion E1 due to the contact with the patient (Step S3).

Furthermore, when an external force due to contact with the patient acts on the distal end portion E1 of the arm portion, an external torque $\tau^{ext}$ based on the external force acts on the joint portion J1 of the arm portion. Furthermore, the disturbance torque $\tau^{dib}$ based on the disturbance acts on the joint portion J1 of the arm portion. A torque obtained by combining the external torque $\tau^{ext}$ based on the external force and the disturbance torque $\tau^{dib}$ based on the disturbance acts on the joint portion J1 of the arm portion.

The disturbance observer calculates a torque estimation value $\tau^{dob}$ ($\tau^{dob}$ added with a caret) estimated to act on the joint portion J1 of the arm portion on the basis of the current value input to the motor of the joint portion J1 and the power value related to the output of the motor of the joint portion J1 (Step S4). Specifically, the disturbance observer estimates a torque estimation value $\hat{\tau}^{dob}$ ($\tau^{dob}$ added with a caret) estimated to have actually acted on the joint portion J1 of the arm portion on the basis of a comparison between a predicted power value by rotation of the joint portion J1 predicted from a current value input to the motor of the joint portion J1 and a power value by actual rotation of the joint portion J1.

The information processing apparatus 100 acquires the detection information and the calculation information from the slave device 20 (Step S5). Specifically, the information processing apparatus 100 acquires the response value $f^{ext}$ of the external force detected by the force sensor FS1 as the detection information. Furthermore, the information processing apparatus 100 acquires, as the calculation information, the torque estimation value $\hat{\tau}^{dob}$ ($\tau^{dob}$ added with a caret) of the joint portion J1 calculated by the disturbance observer.

After acquiring the detection information and the calculation information, the information processing apparatus 100 estimates the disturbance torque estimation value $\hat{\tau}^{dib}$ ($\tau^{dib}$ added with a caret) of the joint portion J1 using the machine learning model M1 (Step S6). Specifically, when acquiring the response value $f^{ext}$ of the external force detected by the force sensor FS1, the information processing apparatus 100 calculates the external torque response value $\tau^{ext}$ acting on the joint portion J1 using the above mathematical expression (2).

Subsequently, the information processing apparatus 100 inputs the torque estimation value $\hat{\tau}^{dob}$ ($\tau^{dob}$ added with a caret) of the joint portion J1 acquired from the disturbance observer and the external torque response value $\tau^{ext}$ calculated using the above mathematical expression (2) to the machine learning model M1, and estimates the disturbance torque estimation value $\hat{\tau}^{dib}$ ($\tau^{dib}$ added with a caret) of the joint portion J1.

After estimating the disturbance torque estimation value $\hat{\tau}^{dib}$ ($\tau^{dib}$ added with a caret) of the joint portion J1, the information processing apparatus 100 estimates the external torque estimation value $\hat{\tau}^{ext}$ ($\tau^{ext}$ added with a caret) estimated to have acted on the joint portion J1 using the above mathematical expression (4) (Step S7).

After calculating the external torque estimation value $\hat{\tau}^{ext}$ ($\tau^{ext}$ added with a caret) of the joint portion J1, the information processing apparatus 100 estimates the external force estimation value $\hat{f}^{ext}$ ($f^{ext}$ added with a caret) estimated to have acted on the distal end portion E1 of the arm portion using the above mathematical expression (5) (Step S8).

After calculating the external force estimation value $\hat{f}^{ext}$ ($f^{ext}$ added with a caret) of the distal end portion E1 of the arm portion, the information processing apparatus 100 transmits information regarding the calculated external force estimation value $\hat{f}^{ext}$ ($f^{ext}$ added with a caret) to the slave device 20 (Step S9).

The slave device 20 feeds back information related to the external force estimation value $\hat{f}^{ext}$ ($f^{ext}$ added with a caret) received from the information processing apparatus 100 to the master device 10.

As described above, the information processing apparatus 100 estimates an external force estimation value which is an estimation value for an external force that acts on an object to be driven (a distal end portion of an arm portion) by performing a process based on a machine learning model with a force estimation value (a torque estimation value) and an external force response value (an external torque response value) as an input, the force estimation value being an estimation value for a force that acts on the object to be driven (each joint portion), the external force response value being based on a value of an external force detected by a force sensor configured to detect the external force that acts on the object to be driven (the distal end portion of the arm portion).

Figure 11:
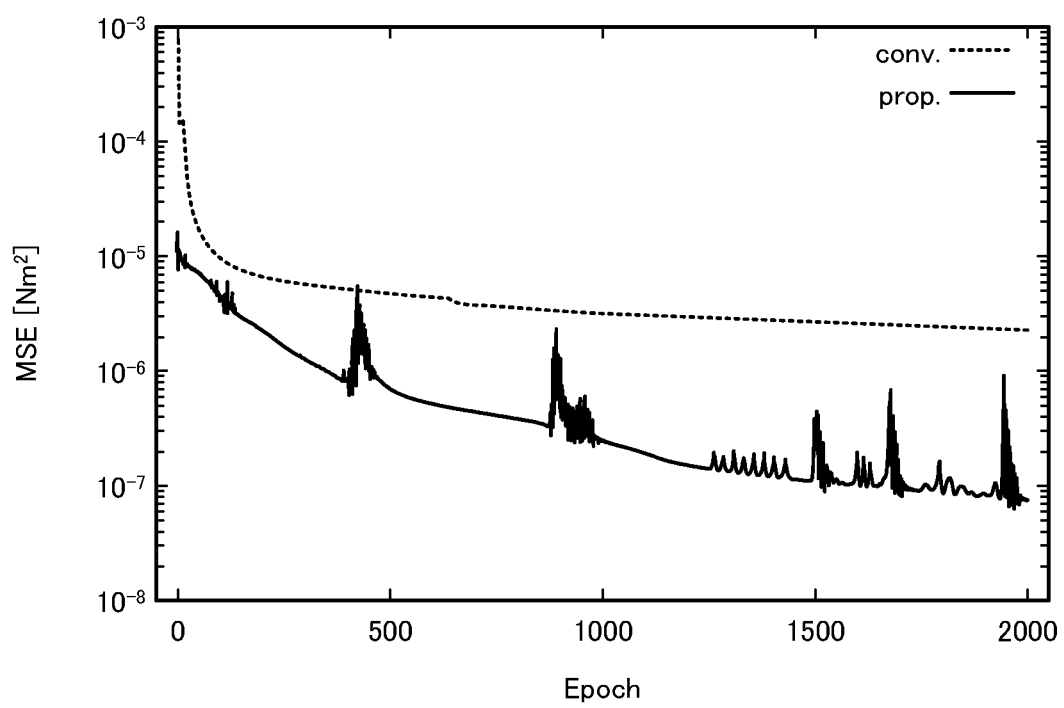
FIG. 11 is a graph illustrating estimation accuracy of a machine learning model according to the embodiment of the present disclosure.

As a result, the information processing apparatus 100 can estimate the disturbance torque estimation value $\hat{\tau}^{dib}$ ($\tau^{dib}$ added with a caret) acting on each joint portion with higher accuracy than the prior art (see FIG. 11). Furthermore, since the information processing apparatus 100 can estimate the disturbance torque estimation value $\hat{\tau}^{dib}$ ($\tau^{dib}$ added with a caret) acting on each joint portion with high accuracy, the external torque estimation value $\hat{\tau}^{ext}$ ($\tau^{ext}$ added with a caret) of each joint portion can be estimated with higher accuracy. Furthermore, since the information processing apparatus 100 can estimate the external torque estimation value $\hat{\tau}^{ext}$ ($\tau^{ext}$ added with a caret) of each joint portion with higher accuracy, the external force estimation value $\hat{f}^{ext}$ ($f^{ext}$ added with a caret) estimated to have acted on the distal end portion E1 of the arm portion can be estimated with higher accuracy.

Note that, in FIGS. 1 and 2, an example in which the slave device 20 and the information processing apparatus 100 are separate devices has been described. However, the slave device 20 and the information processing apparatus 100 may be an integrated device. In a case where the slave device 20 and the information processing apparatus 100 are an integrated device, the calculator (calculation unit 23) of the slave device 20 and a calculation unit 132 of the information processing apparatus 100 function as one calculation unit. Note that the master device 10 may be an integrated device in addition to the slave device 20 and the information processing apparatus 100. Furthermore, the slave device 20, the information processing apparatus 100, and the master device 10 may be controlled by a single PC.

1-4. Configuration of Master Device According to Embodiment

Figure 3:
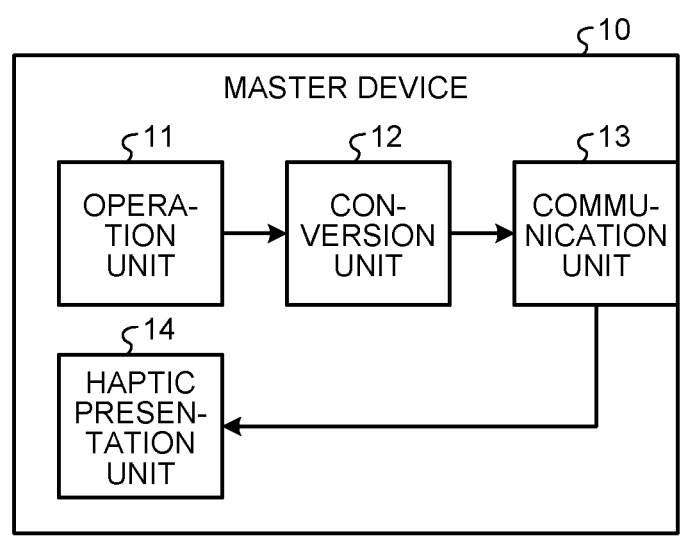
FIG. 3 is a diagram illustrating a configuration example of a master device according to the embodiment of the present disclosure.

Next, a configuration of the master device according to the embodiment of the present disclosure will be described with reference to FIG. 3. FIG. 3 is a diagram illustrating a configuration example of a master device according to the embodiment of the present disclosure.

The master device 10 includes an operation unit 11, a conversion unit 12, a communication unit 13, and a haptic presentation unit 14.

The operation unit 11 includes a master arm or the like for the operator to remotely operate the slave device 20. The operation unit 11 includes, for example, a force sensor that detects an external force acting on the master arm. Furthermore, the operation unit 11 includes, for example, a disturbance observer at each joint portion of the master arm. The operation unit 11 receives an operation input to the arm portion of the slave device 20 by a doctor.

The conversion unit 12 converts operation content performed on the operation unit 11 by the operator into control information for controlling driving of the slave device 20 side (more specifically, drive unit 21 in the slave device 20).

The communication unit 13 is interconnected to the slave device 20 side (more specifically, the communication unit 24 in the slave device 20) via a wireless or wired network. The communication unit 13 transmits the control information output from the conversion unit 12 to the slave device 20.

The haptic presentation unit 14 performs haptic presentation to the operator on the basis of the detection result received by the communication unit 13 from the slave device 20 as feedback information.

The operator who is operating the master device 10 can recognize the contact force applied to the drive unit 21 on the slave device 20 side using the haptic presentation unit 14. For example, in a case where the slave device 20 is a medical robot, an operator such as an operator of a surgical operation obtains a tactile sensation such as a response acting on a medical instrument mounted on the slave device 20 such as a forceps, and thus, it is possible to appropriately perform an action at the time of operating the suture thread and completely end the suture, and it is possible to work efficiently by preventing invasion into living tissue.

1-5. Configuration of Slave Device According to Embodiment

Figure 4:
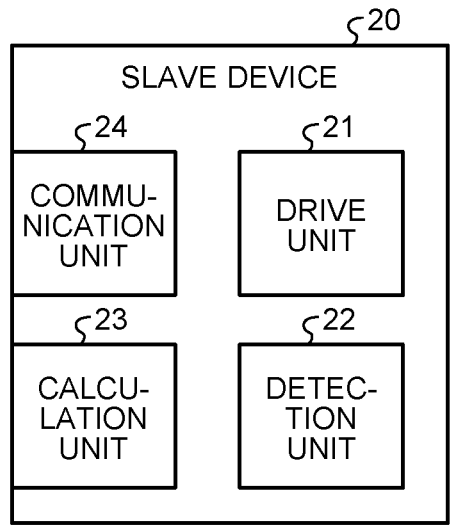
FIG. 4 is a diagram illustrating a configuration example of a slave device according to the embodiment of the present disclosure.

Next, a configuration of the slave device according to the embodiment of the present disclosure will be described with reference to FIG. 4. FIG. 4 is a diagram illustrating a configuration example of the slave device according to the embodiment of the present disclosure.

The slave device 20 includes a drive unit 21, a detection unit 22, the calculation unit 23, and a communication unit 24.

The drive unit 21 moves the object to be driven. The drive unit 21 moves the object to be driven which is a multi-link structure formed by coupling a plurality of links to one another with a joint portion. The drive unit 21 drives the motor to move the object to be driven. In the example illustrated in FIG. 1, the drive unit 21 moves the arm portion.

The drive unit 21 moves the arm portion in accordance with the control information received by the communication unit 24 from the master device 10. The drive unit 21 controls the rotational motion of each joint portion to control the operation of the arm portion. Specifically, the drive unit 21 controls driving of each actuator provided in each joint portion of the arm portion in accordance with control information received by the communication unit 24 from the master device 10 side. The drive unit 21 controls the number of rotations of the motor by controlling the amount of current supplied to the motor in each actuator provided in each joint portion of the arm portion, and controls the rotation angle and the generated torque in each joint portion. The drive unit 21 controls the rotational motion of each joint portion to control the operation of the arm portion. For example, the drive unit 21 moves the arm portion to a position in contact with the patient in accordance with the control information.

The detection unit 22 includes various physical sensors. Specifically, the detection unit 22 includes a force sensor FS1 that detects an external force acting on the arm portion, an encoder built in each actuator provided in each joint portion of the arm portion, and a sensor that measures the attitude, acceleration, angular acceleration, and the like of the arm portion. Furthermore, in a case where a gripping mechanism such as forceps is mounted on the arm portion, the detection unit 22 may include a sensor that detects gripping force.

The detection unit 22 detects a physical state of the slave device 20. The detection unit 22 detects a physical state of the arm portion. The detection unit 22 detects an external force acting on the object to be driven having a joint portion by the force sensor FS1. The detection unit 22 detects an external force acting on a part of the object to be driven. For example, the detection unit 22 detects an external force acting on a portion where the force sensor FS1 is provided. In the example illustrated in FIG. 1, the detection unit 22 detects an external force acting on the distal end portion E1, which is a distal end portion of the arm portion provided with the force sensor FS1. The detection unit 22 detects an external force acting on the distal end portion E1 of the arm portion by contact between the patient and the medical instrument.

In addition, the detection unit 22 detects the rotation angle of the actuator by the encoder. Furthermore, the detection unit 22 may detect a rotation angular velocity of the actuator.

The calculation unit 23 corresponds to a disturbance observer (calculator). The calculation unit 23 calculates a torque estimation value that is an estimation value of the torque acting on each joint portion on the basis of the current value input to the motor of each joint portion and the power value related to the output of the motor. In this manner, the calculation unit 23 calculates a force estimation value (torque estimation value) that is an estimation value of the force acting on the object to be driven (each joint portion) on the basis of the input value input to the motor and the output value related to the output of the motor.

The communication unit 24 is interconnected to the master device 10 side (more specifically, the communication unit 13 in the master device 10) via a wireless or wired network. The communication unit 24 receives control information corresponding to the operation content received from the operator from the master device 10. Furthermore, the communication unit 24 transmits the detection result by the detection unit 22 and the calculation result by the calculation unit 23 to the master device 10 side (including the information processing apparatus 100).

Figure 5:
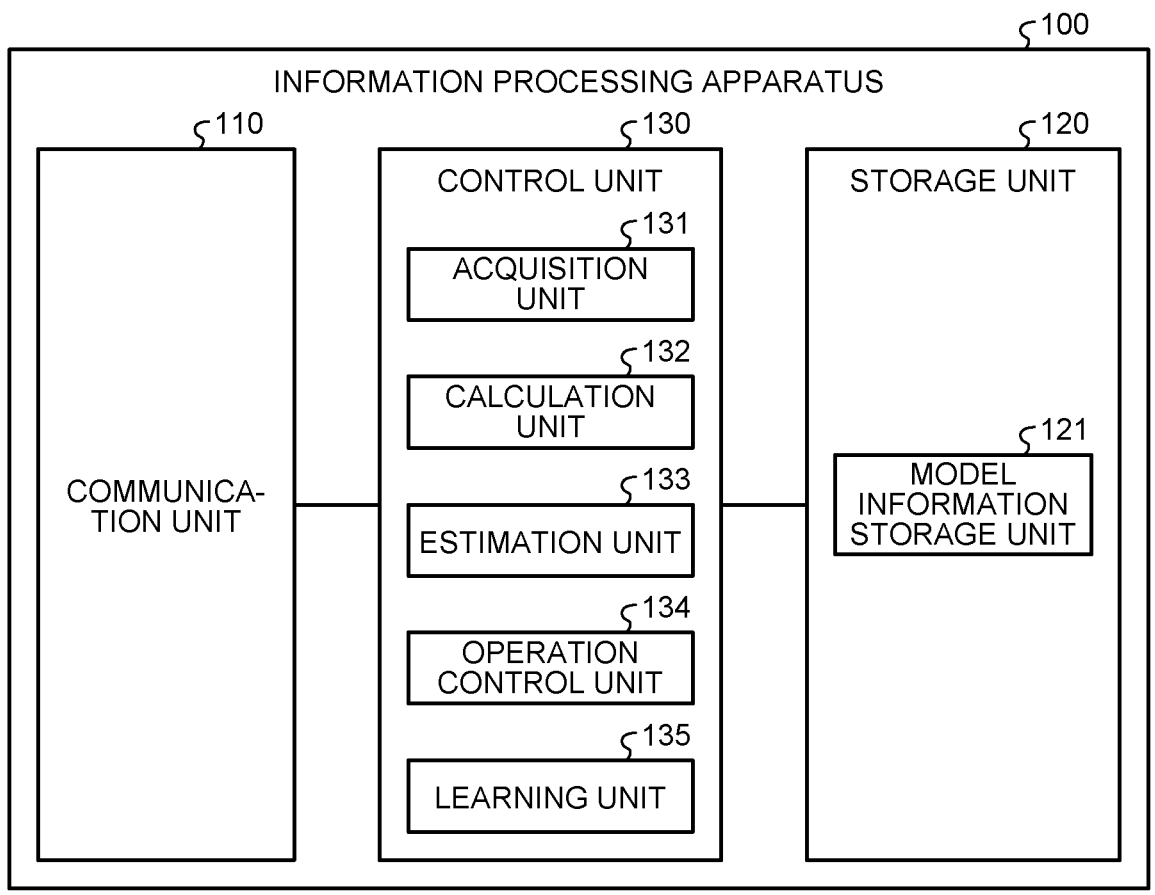
FIG. 5 is a diagram illustrating a configuration example of an information processing apparatus according to the embodiment of the present disclosure.

1-6. Configuration of Information Processing Apparatus According to Embodiment Next, a configuration of an information processing apparatus according to the embodiment of the present disclosure will be described with reference to FIG. 5. FIG. 5 is a diagram illustrating a configuration example of an information processing apparatus according to the embodiment of the present disclosure.

As illustrated in FIG. 5, the information processing apparatus 100 includes a communication unit 110, a storage unit 120, and a control unit 130.

The communication unit 110 is implemented by, for example, an NIC or the like. Then, the communication unit 110 is connected to the network N in a wired or wireless manner, and transmits and receives information to and from the master device 10 and the slave device 20.

The storage unit 120 is implemented by, for example, a semiconductor memory element such as a random access memory (RAM) or a flash memory, or a storage device such as a hard disk or an optical disk. For example, the storage unit 120 stores an information processing program according to the embodiment. As illustrated in FIG. 5, the storage unit 120 includes a model information storage unit 121.

Figure 6:
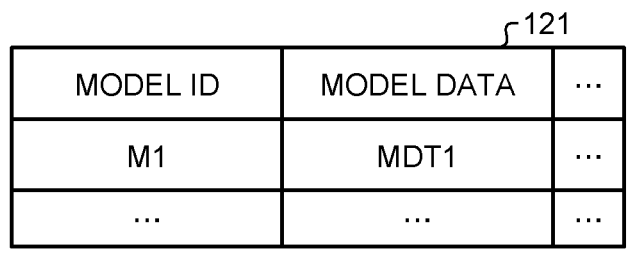
FIG. 6 is a diagram illustrating an example of a model information storage unit according to the embodiment of the present disclosure.

The model information storage unit 121 stores various types of information regarding the machine learning model. FIG. 6 is a diagram illustrating an example of the model information storage unit according to the embodiment of the present disclosure. In the example illustrated in FIG. 6, the model information storage unit 121 includes items such as "model ID" and "model data".

The "model ID" indicates identification information for identifying the machine learning model. The "model data"

indicates model data of the machine learning model. For example, the "model data" stores data for estimating a disturbance torque estimation value $\hat{\tau}^{dib}$ ($\tau^{dib}$ added with a caret), which is an estimation value of the disturbance torque based on the disturbance acting on each joint portion Ji, on the basis of the torque estimation value $\hat{\tau}^{dob}$ ($\tau^{dob}$ added with a caret) calculated by the disturbance observer and the external torque response value $\tau^{ext}$ of each joint portion Ji calculated on the basis of the response value $f^{ext}$ of the external force detected by the force sensor FS1.

In the example illustrated in the first record of FIG. 6, the model identified by the model ID "M1" corresponds to the machine learning model M1. In addition, the model data "MDT1" indicates model data (see, for example, FIG. 8.) of the machine learning model M1 to be described later.

Here, it is assumed that the model data MDT1 is implemented by a regression model indicated by "y=a1*x1+a2*x2+ . . . +ai*xi". In this case, the first element included in the model data MDT1 corresponds to the input data (xi) such as x1 and x2. Further, the weight of the first element corresponds to the coefficient ai corresponding to xi. Here, the regression model can be regarded as a simple perceptron having an input layer and an output layer. When each model is regarded as the simple perceptron, the first element can be regarded as any node included in the input layer, and the second element can be regarded as a node included in the output layer.

In addition, it is assumed that the model data MDT1 is implemented by a neural network having one or a plurality of intermediate layers such as a deep neural network (DNN). In this case, the first element included in the model data MDT1 corresponds to any node included in the input layer or the intermediate layer. In addition, the second element corresponds to a node at a next stage which is a node to which a value is transmitted from a node corresponding to the first element. In addition, the weight of the first element corresponds to a connection coefficient that is a weight considered for a value transmitted from the node corresponding to the first element to the node corresponding to the second element.

The information processing apparatus 100 estimates the disturbance torque estimation value $\hat{\tau}^{dib}$ ($\tau^{dib}$ added with a caret) of each joint portion using a model having an arbitrary structure such as the regression model or the neural network described above. Specifically, in the model data MDT1, when the torque estimation value $\hat{\tau}^{dob}$ ($\tau^{dob}$ added with a caret) of each joint portion and the external torque response value $\tau^{ext}$ of each joint portion are input, a coefficient is set such that the disturbance torque estimation value $\hat{\tau}^{dib}$ ($\tau^{dib}$ added with a caret) of each joint portion is output. The information processing apparatus 100 calculates the disturbance torque estimation value $\hat{\tau}^{dib}$ ($\tau^{dib}$ added with a caret) of each joint portion using such model data MDT1.

Furthermore, in a case where the information processing apparatus 100 performs estimation processing using generative adversarial networks (GAN), the model data MDT1 may be a model constituting a part of the GAN.

1-6-1. Configuration of Control Unit According to Embodiment

The control unit 130 is implemented by executing various programs (corresponding to an example of an information processing program) stored in a storage device inside the information processing apparatus 100 using a RAM as a work area by a central processing unit (CPU), a micro processing unit (MPU), or the like. Furthermore, the control unit 130 is implemented by, for example, an integrated circuit such as an application specific integrated circuit (ASIC) or a field programmable gate array (FPGA).

As illustrated in FIG. 5, the control unit 130 includes an acquisition unit 131, the calculation unit 132, an estimation unit 133, an operation control unit 134, and a learning unit 135, and realizes or executes a function and an action of information processing described below. Note that the internal configuration of the control unit 130 is not limited to the configuration illustrated in FIG. 5, and may be another configuration as long as information processing to be described later is performed.

The acquisition unit 131 acquires the detection information and the calculation information from the slave device 20. Specifically, the acquisition unit 131 acquires the response value $f^{ext}$ of the external force detected by the force sensor FS1 as the detection information. The acquisition unit 131 acquires the external force acting on the distal end portion E1 of the arm portion detected by the force sensor FS1. In addition, the acquisition unit 131 acquires the torque estimation value $\hat{\tau}^{dob}$ ($\tau^{dob}$ added with a caret) of each joint portion calculated by the calculation unit 23 as the calculation information.

In addition, the acquisition unit 131 acquires the machine learning model learned by the learning unit 135. When acquiring the machine learning model, the acquisition unit 131 stores the acquired machine learning model in the model information storage unit 121.

When the response value $f^{ext}$ of the external force is acquired by the acquisition unit 131, the calculation unit 132 calculates the external torque response value $\tau^{ext}$ of each joint portion by multiplying the response value $f^{ext}$ of the external force detected by the force sensor FS1 and the transposed matrix $J^T_{aco}$ of the Jacobian matrix $J_{aco}$ using the above mathematical expression (2).

When the external torque response value $\tau^{ext}$ of each joint portion is calculated by the calculation unit 132, the estimation unit 133 refers to the model information storage unit 121 and acquires the machine learning model M1. Subsequently, when acquiring the machine learning model M1, the estimation unit 133 inputs the torque estimation value $\hat{\tau}^{dob}$ ($\tau^{dob}$ added with a caret) of each joint portion acquired by the acquisition unit 131 and the external torque response value $\tau^{ext}$ of each joint portion calculated by the calculation unit 132 to the machine learning model M1, thereby estimating the disturbance torque estimation value $\hat{\tau}^{dib}$ ($\tau^{dib}$ added with a caret) of each joint portion.

The estimation unit 133 estimates the external force estimation value using a machine learning model having a function of long short-term memory (LSTM). For example, the estimation unit 133 estimates the disturbance torque estimation value $\hat{\tau}^{dib}$ ($\tau^{dib}$ added with a caret) of each joint portion using the machine learning model illustrated in FIG. 8.

Subsequently, after estimating the disturbance torque estimation value $\hat{\tau}^{dib}$ ($\tau^{dib}$ added with a caret) of each joint portion, the estimation unit 133 calculates the external torque estimation value $\hat{\tau}^{ext}$ ($\tau^{ext}$ added with a caret) of each joint portion by subtracting the estimated disturbance torque estimation value $\hat{\tau}^{dib}$ ($\tau^{dib}$ added with a caret) of each joint portion from the torque estimation value $\hat{\tau}^{dob}$ ($\tau^{dob}$ added with a caret) of each joint portion acquired by the acquisition unit 131 using the above mathematical expression (4).

Subsequently, after calculating the external torque estimation value $\hat{\tau}^{ext}$ ($\tau^{ext}$ added with a caret) of each joint portion, the estimation unit 133 calculates the external force estimation value $\hat{f}^{ext}$ ($f^{ext}$ added with a caret) estimated to have acted on the distal end portion E1 of the arm portion by multiplying the inverse transposed matrix $J^{-T}{}_{aco}$ of the Jacobian matrix $J_{aco}$ by the calculated external torque estimation value $\tau^{ext}$ ($\tau^{ext}$ added with a caret) of each joint portion Ji using the above mathematical expression (5).

In this manner, the estimation unit 133 estimates an external force estimation value which is an estimation value for an external force that acts on an object to be driven (distal end portion of an arm portion) by performing a process based on a machine learning model with a force estimation value (torque estimation value) and an external force response value (external torque response value) as an input, the force estimation value being an estimation value for a force that acts on the object to be driven (each joint portion), the external force response value being based on a value of an external force detected by a force sensor configured to detect the external force that acts on the object to be driven (distal end portion of the arm portion). Specifically, the machine learning model includes a neural network computational model learned, on the basis of a force estimation value (a torque estimation value) which is an estimation value for a force that acts on the object to be driven (each joint portion) and an external force response value (an external torque response value) based on the value of the external force detected by the force sensor, so as to estimate an disturbance estimation value (disturbance torque estimation value) which is an estimation value regarding a disturbance that acts on the object to be driven (each joint portion), and the estimation unit 133 estimates the external force estimation value on the basis of a value obtained by subtracting the disturbance estimation value (the disturbance torque estimation value) estimated using the machine learning model from the force estimation value (the torque estimation value).

For example, the object to be driven (slave device 20) includes one or more joint portions configured to be rotated by being driven by a motor, the force sensor detects an external force that acts on the object to be driven including the one or more joint portions, the force estimation value includes a torque estimation value which is an estimation value for a torque that acts on the one or more joint portions, the external force response value includes an external torque response value of the one or more joint portions, and the external torque response value is determined on the basis of the value of the external force, and the estimation unit 133 estimates the external force estimation value by inputting the torque estimation value and the external torque response value to the machine learning model. Specifically, the machine learning model includes a neural network computational model learned, on the basis of a torque estimation value which is an estimation value for a force that acts on the object to be driven (each joint) and an external torque response value based on the value of the external force detected by the force sensor, so as to estimate a disturbance torque estimation value which is an estimation value regarding a disturbance that acts on the object to be driven (each joint), and the estimation unit 133 estimates the external force estimation value on the basis of a value obtained by subtracting the disturbance torque estimation value estimated using the machine learning model from the torque estimation value.

For example, using the above mathematical expression (5), the estimation unit 133 estimates the external force estimation value by performing coordinate transformation, from a joint space value to an operation space value, on the value obtained by subtracting the disturbance torque estimation value estimated using the machine learning model from the torque estimation value.

After the external force estimation value $f^{ext}$ ($f^{ext}$ added with a caret) of the distal end portion E1 of the arm portion is calculated by the estimation unit 133, the operation control unit 134 transmits information regarding the external force estimation value $f^{ext}$ ($f^{ext}$ added with a caret) calculated by the estimation unit 133 to the slave device 20.

In a case where the torque estimation value $\tau^{dob}$ ($\tau^{dob}$ added with a caret) of each joint portion calculated by the calculation unit 23 and the external torque response value $\tau^{ext}$ of each joint portion calculated on the basis of the value of the external force detected by the force sensor are input as inputs of the machine learning model M1, the learning unit 135 causes the machine learning model M1 to learn such that the disturbance torque estimation value $\tau^{dib}$ ($\tau^{dib}$ added with a caret) of each joint portion calculated by subtracting the external torque response value $\tau^{ext}$ of each joint portion from the torque estimation value $\tau^{dob}$ ($\tau^{dob}$ added with a caret) of each joint portion using the above mathematical expression (3) is output as an output of the machine learning model M1.

As described above, the learning unit 135 learns the machine learning model that estimates the disturbance estimation value (disturbance torque estimation value) on the basis of the learning data including the force estimation value (torque estimation value) that is the estimation value of the force acting on the object to be driven (each joint portion) and the external force response value (external torque response value) based on the value of the external force detected by the force sensor. That is, the learning unit 135 learns the machine learning model that estimates the disturbance torque estimation value for each joint portion on the basis of learning data including the torque estimation value for each joint portion and the external torque response value for each joint portion. Specifically, the learning unit 135 learns the machine learning model for estimating a disturbance estimation value (disturbance torque estimation value), which is an estimation value regarding a disturbance acting on the object to be driven, on the basis of learning data including the first force estimation value (first torque estimation value) calculated by the calculation unit 23 of the slave device 20 and the first external force response value (first external torque response value) based on the value of the external force detected by the force sensor FS1. More specifically, the learning unit 135 learns the machine learning model for estimating the disturbance torque estimation value $\tau^{dib}$ ($\tau^{dib}$ added with a caret) of each joint portion on the basis of the torque estimation value $\tau^{dob}$ ($\tau^{dob}$ added with a caret) of each joint portion calculated by the calculation unit 23 and the external torque response value $\tau^{ext}$ of each joint portion calculated on the basis of the value of the external force detected by the force sensor FS1. The estimation unit 133 estimates the external force estimation value using the machine learning model learned by the learning unit 135.

1-7. Details of Information Processing According to Embodiment

Next, various types of information processing according to the embodiment will be described in more detail with reference to FIGS. 7 to 11.

1-7-1. Example of Learning Processing According to Embodiment

Figure 7:
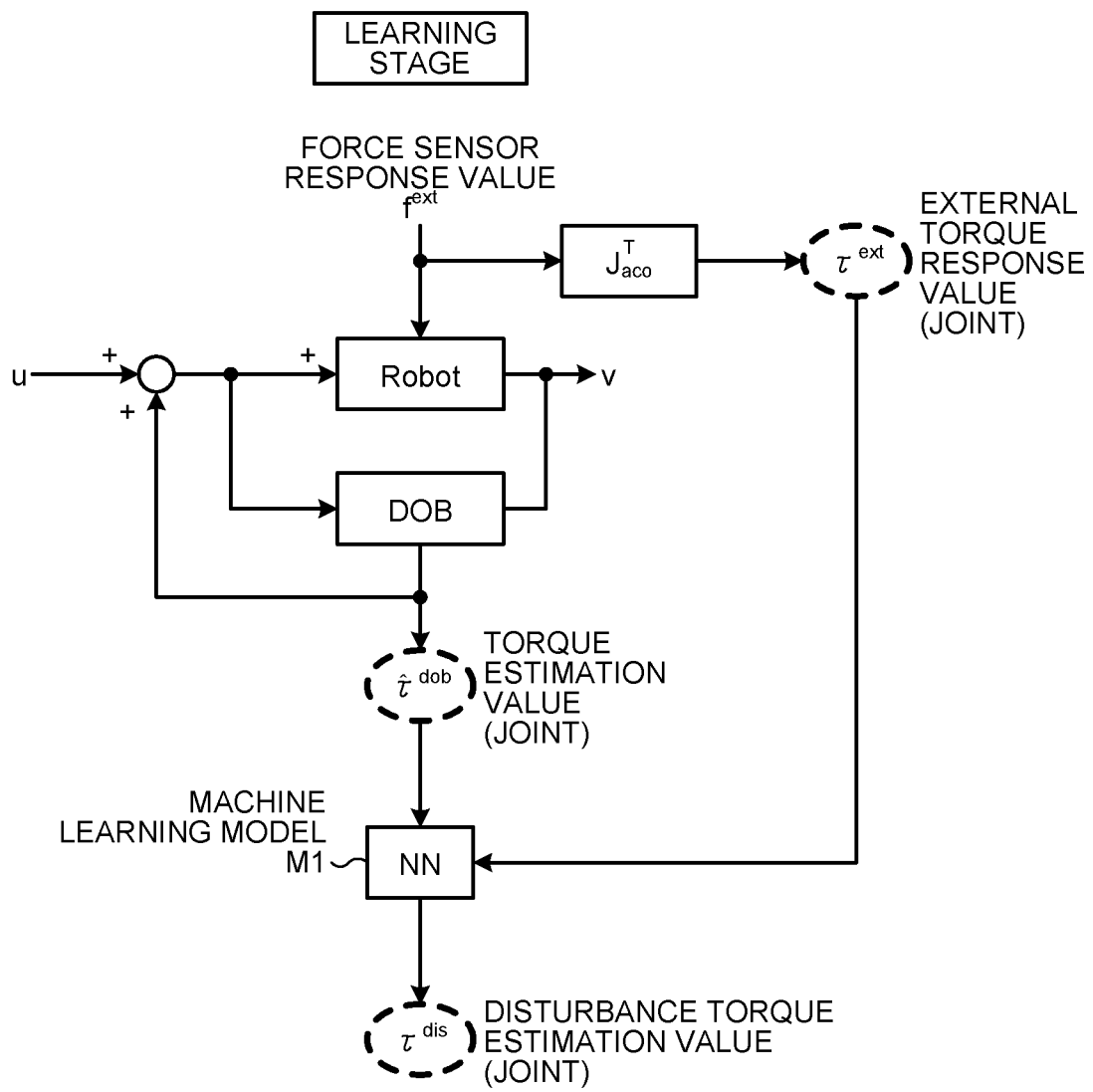
FIG. 7 is a diagram illustrating an example of learning processing according to the embodiment of the present disclosure.

First, an example of learning processing according to the embodiment of the present disclosure will be described with reference to FIG. 7. FIG. 7 is a diagram illustrating an example of learning processing according to the embodiment of the present disclosure. Specifically, FIG. 7 is a block diagram illustrating a functional configuration example in a learning stage of the information processing system 1 according to the embodiment of the present disclosure. In FIG. 7, a block denoted as Robot indicates the slave device 20. Blocks denoted by DOB indicate disturbance observers (calculators). Furthermore, a block described as NN indicates the machine learning model M1.

As illustrated in FIG. 7, when the response value $f^{ext}$ of the external force detected by the force sensor FS1 is acquired by the acquisition unit 131, the calculation unit 132 calculates the external torque response value $\tau^{ext}$ of each joint portion by multiplying the response value $f^{ext}$ of the external force detected by the force sensor FS1 and the transposed matrix $J^T_{aco}$ of the Jacobian matrix $J_{aco}$ using the above mathematical expression (2).

In addition, the calculation unit 23 calculates a torque estimation value $\tau^{dob}$ ($\tau^{dob}$ added with a caret) of each joint portion on the basis of the current value u input to the motor of each joint portion and the power value v related to the output of the motor.

In a case where the calculated external torque response value $\tau^{ext}$ of each joint portion and the torque estimation value $\tau^{dob}$ of each joint portion ($\tau^{dob}$ added with a caret) are input as the input information of the machine learning model M1, the learning unit 135 causes the machine learning model M1 to learn such that the disturbance torque estimation value $\tau^{dib}$ ($\tau^{dib}$ added with a caret) of each joint portion calculated by subtracting the external torque response value $\tau^{ext}$ of each joint portion from the torque estimation value $\tau^{dob}$ of each joint portion ($\tau^{dob}$ added with a caret) using the above mathematical expression (3) is output as the output information of the machine learning model M1.

1-7-2. Configuration Example of Machine Learning Model

Figure 8:
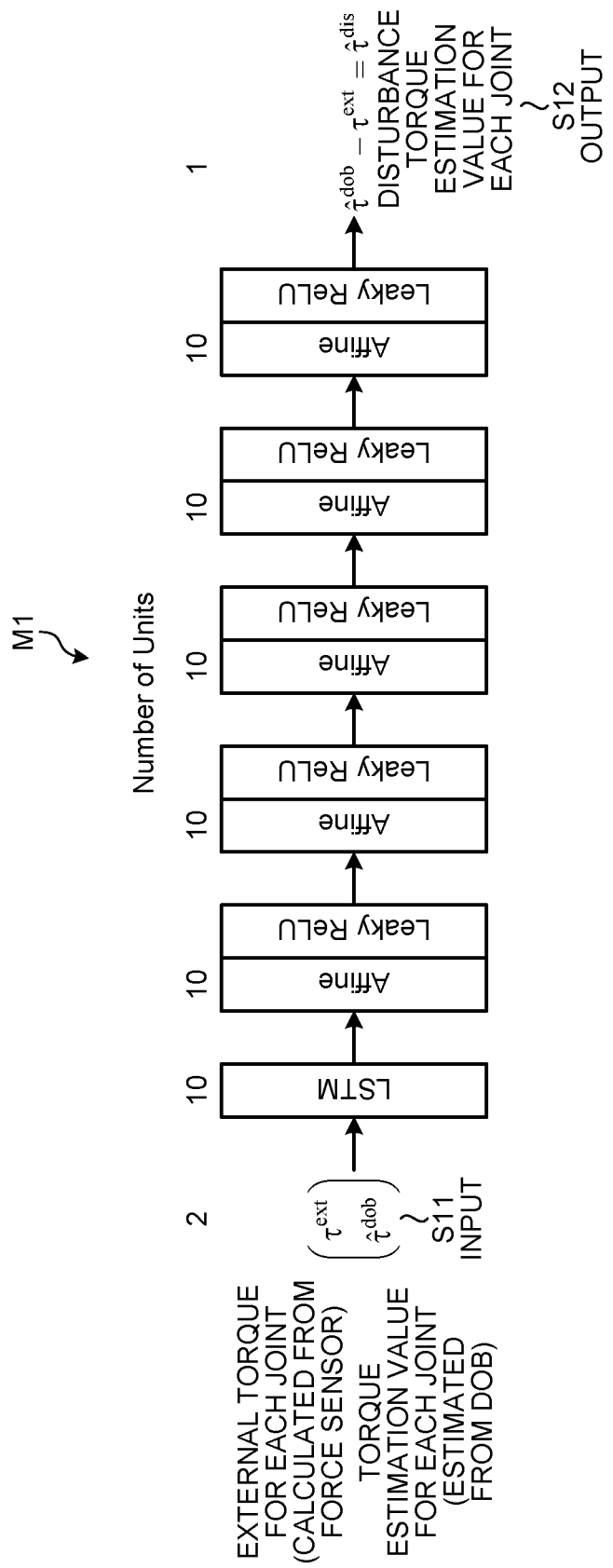
FIG. 8 is a diagram illustrating an example of a machine learning model according to the embodiment of the present disclosure.

Next, an example of a machine learning model according to the embodiment will be described with reference to FIG. 8. FIG. 8 is a diagram illustrating an example of the machine learning model according to the embodiment of the present disclosure. As illustrated in FIG. 8, the machine learning model M1 according to the embodiment of the present disclosure includes a deep neural network in which a long short-term memory (LSTM) block strong for time-series data and a normal feedforward layer are combined. FIG. 8 illustrates a learning stage of the machine learning model M1.

As illustrated in FIG. 8, the external torque response value $\tau^{ext}$ for each joint portion calculated on the basis of the response value $f^{feat}$ of the external force detected by the force sensor FS1 and the torque estimation value $\tau^{dob}$ ($\tau^{dob}$ added with a caret) for each joint portion estimated by the disturbance observer are input to the input layer of the machine learning model M1 (Step S11).

In addition, the machine learning model M1 is caused to learn such that the disturbance torque estimation value $\tau^{dib}$ ($\tau_{dib}$ added with a caret) for each joint portion calculated by subtracting the external torque response value $\tau^{ext}$ for each joint portion from the torque estimation value $\tau^{dob}$ ($\tau^{dob}$ added with a caret) for each joint portion using the above mathematical expression (3) is output from the output layer of the machine learning model M1 (Step S12).

1-7-3. Example of Learning Data

Figure 9:
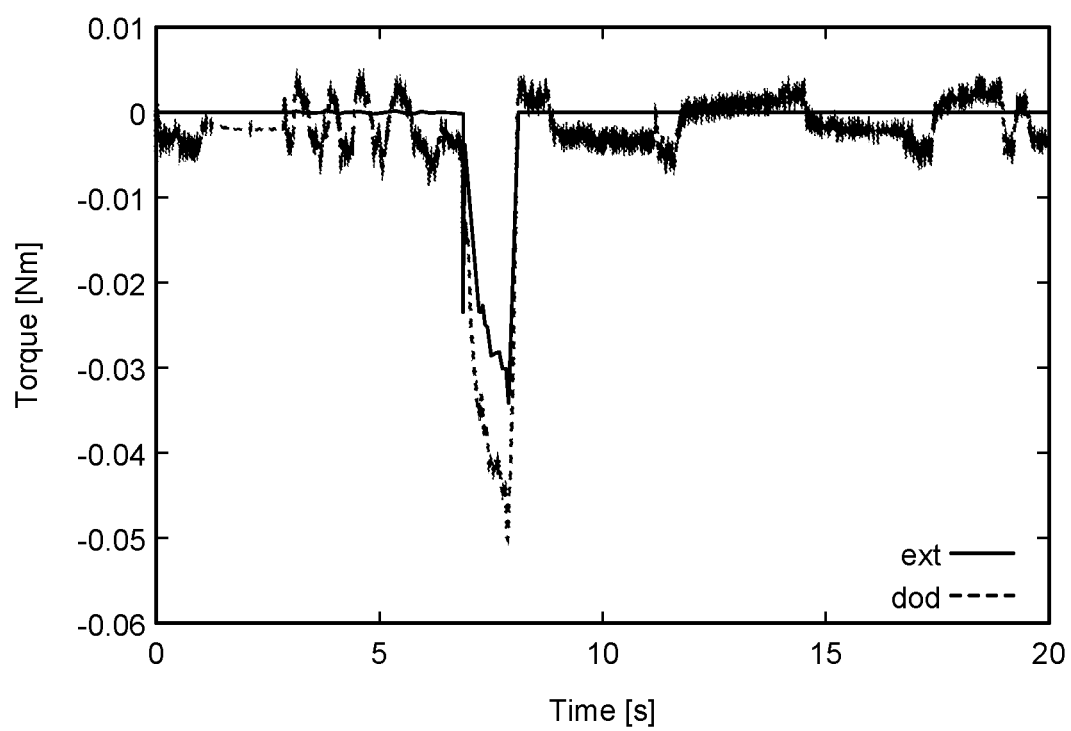
FIG. 9 is a diagram illustrating an example of learning data according to the embodiment of the present disclosure.

Next, an example of learning data according to the embodiment of the present disclosure will be described with reference to FIG. 9. FIG. 9 is a graph diagram illustrating an example of learning data according to the embodiment of the present disclosure. FIG. 9 is a graph diagram illustrating an example of learning data of the machine learning model M1 according to the embodiment of the present disclosure. In the graph of FIG. 9, the horizontal axis represents time (seconds), and the vertical axis represents torque (N·m) of the joint portion.

A solid line of the learning data illustrated in FIG. 9 indicates time-series data of the external torque response value $\tau^{ext}$ of the joint portion calculated on the basis of the response value $f^{ext}$ of the external force detected by the force sensor FS1. In addition, a dotted line of the learning data illustrated in FIG. 9 indicates a torque estimation value $\tau^{dob}$ ($\tau^{rob}$ added with a caret) of the joint portion estimated by the disturbance observer.

In the example illustrated in FIG. 9, during 0 to 7 (seconds), the machine learning model M1 is caused to learn learning data in a state where the arm portion is freely operated. That is, the learning unit 135 causes, during 0 to 7 (seconds), the machine learning model M1 to learn learning data in the no-load state in which the force sensor is not in contact with the contact target.

Subsequently, in the example illustrated in FIG. 9, during 7 to 8 (seconds), the machine learning model M1 is caused to learn learning data in a state where the arm portion is brought into contact with the contact target. That is, the learning unit 135 causes, during 7 to 8 (seconds), the machine learning model M1 to learn learning data in a load state in which the force sensor is in contact with the contact target.

Subsequently, in the example illustrated in FIG. 9, during 8 to 20 (seconds), the machine learning model M1 is caused to learn learning data in a state where the arm portion is freely operated. That is, the learning unit 135 causes, during 8 to 20 (seconds), the machine learning model M1 to learn learning data in the no-load state in which the force sensor is not in contact with the contact target.

As described above, the learning unit 135 learns the machine learning model on the basis of the learning data including the combination of the first learning data in the load state in which the force sensor is in contact with the contact target and the second learning data in the no-load state in which the force sensor is not in contact with the contact target.

1-7-4. Example of Estimation Processing According to Embodiment

Figure 10:
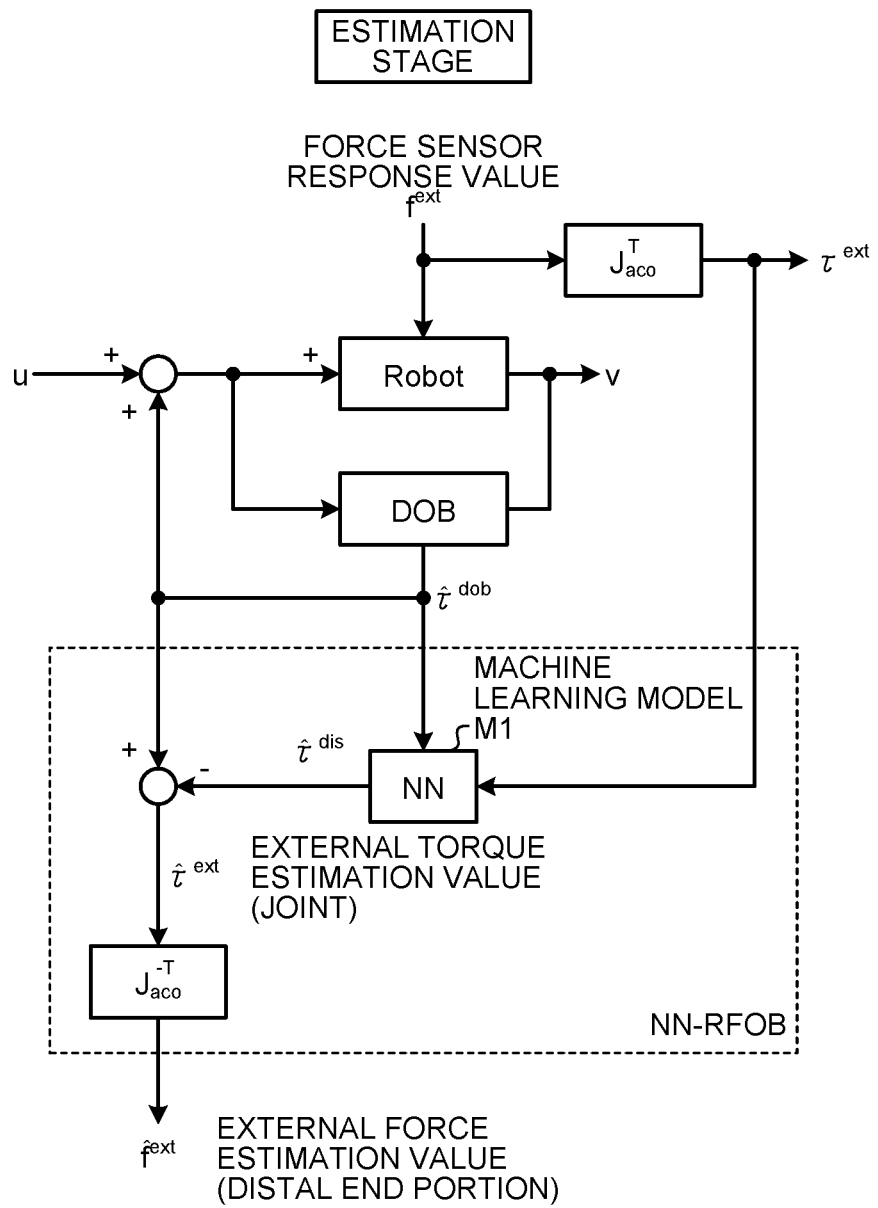
FIG. 10 is a diagram illustrating an example of estimation processing according to the embodiment of the present disclosure.

Next, an example of estimation processing according to the embodiment of the present disclosure will be described with reference to FIG. 10. FIG. 10 is a diagram illustrating an example of estimation processing according to the embodiment of the present disclosure. Specifically, FIG. 10 is a block diagram illustrating a functional configuration example in the estimation stage of the information processing system according to the embodiment of the present disclosure. In FIG. 10, a block denoted as Robot indicates the slave device 20. Blocks denoted by DOB indicate disturbance observers (calculators). Furthermore, a block described as NN indicates the learned machine learning model M1.

As illustrated in FIG. 10, when the response value $f^{ext}$ of the external force detected by the force sensor FS1 is acquired by the acquisition unit 131, the calculation unit 132 calculates the external torque response value $\tau^{ext}$ of each joint portion by multiplying the response value $f^{ext}$ of the external force detected by the force sensor FS1 and the transposed matrix $J^T_{aco}$ of the Jacobian matrix $J_{aco}$ using the above mathematical expression (2).

In addition, a calculation unit 32 calculates a torque estimation value $\hat{\tau}^{dob}$ ($\tau^{dob}$ added with a caret) of each joint portion on the basis of the current value u input to the motor of each joint portion and the power value v related to the output of the motor.

The estimation unit 133 inputs the external torque response value $\tau^{ext}$ of each joint portion calculated by the calculation unit 132 and the torque estimation value $\hat{\tau}^{dob}$ ($\tau^{dob}$ added with a caret) of each joint portion calculated by the calculation unit 32 to the learned machine learning model M1, thereby estimating the disturbance torque estimation value $\hat{\tau}^{dib}$ ($\tau^{dib}$ added with a caret) of each joint portion.

Subsequently, after estimating the disturbance torque estimation value $\hat{\tau}^{dib}$ ($\tau^{dib}$ added with a caret) of each joint portion using the machine learning model M1, the estimation unit 133 calculates the external torque estimation value $\hat{\tau}^{ext}$ ($\tau^{ext}$ added with a caret) of each joint portion by subtracting the estimated disturbance torque estimation value $\hat{\tau}^{dib}$ ($\tau^{dib}$ added with a caret) of each joint portion from the torque estimation value $\hat{\tau}^{dob}$ ($\tau^{dob}$ added with a caret) of each joint portion calculated by the disturbance observer.

Subsequently, after calculating the external torque estimation value $\hat{\tau}^{ext}$ ($\tau^{ext}$ added with a caret) of each joint portion, the estimation unit 133 calculates the external force estimation value $\hat{f}^{ext}$ ($f^{ext}$ added with a caret) estimated to have acted on the distal end portion E1 of the arm portion by multiplying the inverse transposed matrix $J^{-T}_{aco}$ of the Jacobian matrix $J_{aco}$ by the calculated external torque estimation value $\hat{\tau}^{ext}$ ($\tau^{ext}$ added with a caret) of each joint portion Ji using the above mathematical expression (5).

1-7-5. Estimation Accuracy of Machine Learning Model

Next, estimation accuracy of a machine learning model according to the embodiment of the present disclosure will be described with reference to FIG. 11. FIG. 11 is a graph illustrating estimation accuracy of the machine learning model according to the embodiment of the present disclosure. In the graph of FIG. 11, the horizontal axis represents the number of epochs, and the vertical axis represents a mean square error.

A solid line in the graph in FIG. 11 indicates the estimation accuracy of the machine learning model according to the embodiment of the present disclosure. In addition, a dotted line in the graph of FIG. 11 indicates the estimation accuracy of the machine learning model according to the prior art. Here, the machine learning model according to the prior art estimates the external force estimation value $\hat{f}^{ext}$ ($f^{ext}$ added with a caret) estimated to have acted on the distal end portion E1 of the arm portion using the position information and the speed information of the robot apparatus as the input information of the machine learning model.

As illustrated in FIG. 11, a comparison result has been obtained indicating that the machine learning model (solid line) according to the embodiment of the present disclosure has a smaller error and higher accuracy than the machine learning model (dotted line) according to the prior art.

1-8. Procedure of Information Processing According to Embodiment

Next, a procedure of various types of information processing according to the embodiment will be described with reference to FIGS. 12 to 13. Note that the processing of each step in FIGS. 12 and 13 may be performed by any device included in the information processing system 1, such as the information processing apparatus 100 and the slave device 20.

1-8-1. Procedure of Learning Processing According to Embodiment

First, a process of learning processing according to the embodiment of the present disclosure will be described with reference to FIG. 12. FIG. 12 is a flowchart illustrating a procedure of learning processing according to the embodiment of the present disclosure.

Figure 12:
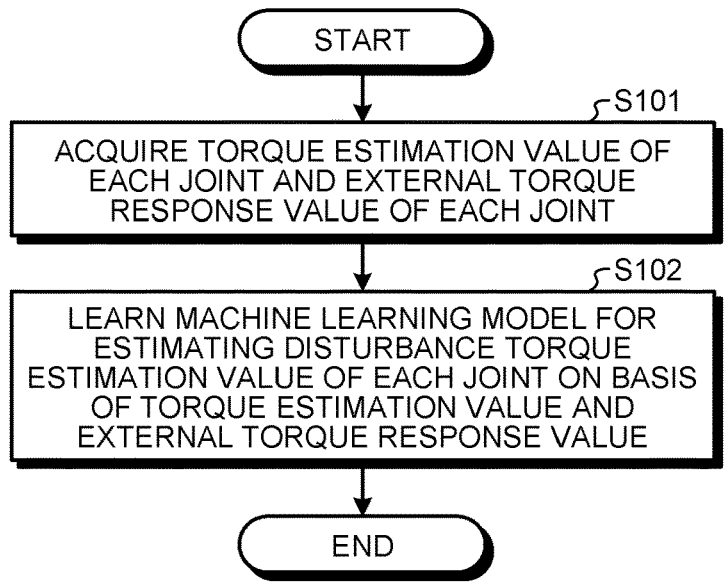
FIG. 12 is a flowchart illustrating a procedure of learning processing according to the embodiment of the present disclosure.

As illustrated in FIG. 12, the information processing system 1 acquires the torque estimation value of each joint of the robot apparatus and the external torque response value of each joint (Step S101). For example, the information processing apparatus 100 acquires the torque estimation value of each joint of the slave device 20 and the external torque response value of each joint.

Subsequently, the information processing system 1 learns a machine learning model for estimating the disturbance torque estimation value of each joint on the basis of the torque estimation value of each joint and the external torque response value of each joint (Step S102). For example, the information processing apparatus 100 learns the machine learning model M1 for estimating the disturbance torque estimation value of each joint of the slave device 20 on the basis of the torque estimation value of each joint of the slave device 20 and the external torque response value of each joint.

1-8-2. Procedure of Estimation Processing According to Embodiment

Next, a process of estimation processing according to the embodiment of the present disclosure will be described with reference to FIG. 13. FIG. 13 is a flowchart illustrating a procedure of estimation processing according to the embodiment of the present disclosure.

Figure 13:
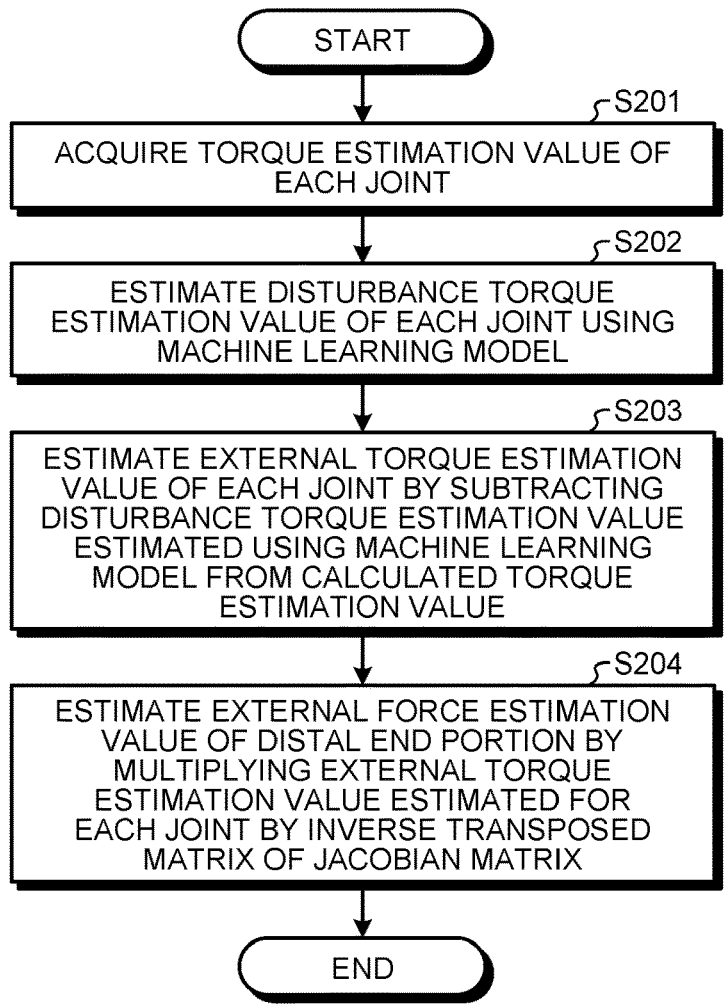
FIG. 13 is a flowchart illustrating a procedure of estimation processing according to the embodiment of the present disclosure.

As illustrated in FIG. 13, the information processing system 1 acquires a torque estimation value of each joint of the robot apparatus (Step S201). For example, the information processing apparatus 100 acquires the torque estimation value of each joint of the slave device 20.

Subsequently, the information processing system 1 estimates a disturbance torque estimation value of each joint using the machine learning model (Step S202). For example, the information processing apparatus 100 estimates the disturbance torque estimation value of each joint of the slave device 20 using the machine learning model M1.

Subsequently, the information processing system 1 estimates the external torque estimation value of each joint by subtracting the disturbance torque estimation value estimated using the machine learning model from the calculated torque estimation value (Step S203). For example, the information processing apparatus 100 estimates the external torque estimation value of each joint of the slave device 20 by subtracting the disturbance torque estimation value of each joint of the slave device 20 estimated using the machine learning model M1 from the calculated torque estimation value of each joint of the slave device 20.

Subsequently, the information processing system 1 estimates the external force estimation value of the distal end portion of the robot apparatus by multiplying the external torque estimation value estimated for each joint by the inverse transposed matrix of the Jacobian matrix (Step S204). For example, the information processing apparatus 100 estimates the external force estimation value of the distal end portion E1 of the slave device 20 by multiplying the external torque estimation value of each joint estimated for each joint of the slave device 20 by the inverse transposed matrix of the Jacobian matrix.

1-9. Modification of Embodiment

Next, various types of information processing according to a modification of the present disclosure will be described with reference to FIGS. 14 to 15.

1-9-1. First Modification of Embodiment

First, an example of information processing according to the first modification of the present disclosure will be described with reference to FIG. 14. FIG. 14 is a diagram illustrating an example of information processing according to the first modification of the present disclosure. The example illustrated in FIG. 14 is different from the embodiment in that only the torque estimation value $\tau^{dob}$ ($\tau^{dob}$ added with a caret) of each joint portion calculated by the disturbance observer is used as the input information of the machine learning model M1 in the estimation stage, and the external torque response value $\tau^{ext}$ of each joint portion calculated on the basis of the external force detected by the force sensor FS1 is not used.

Figure 14:
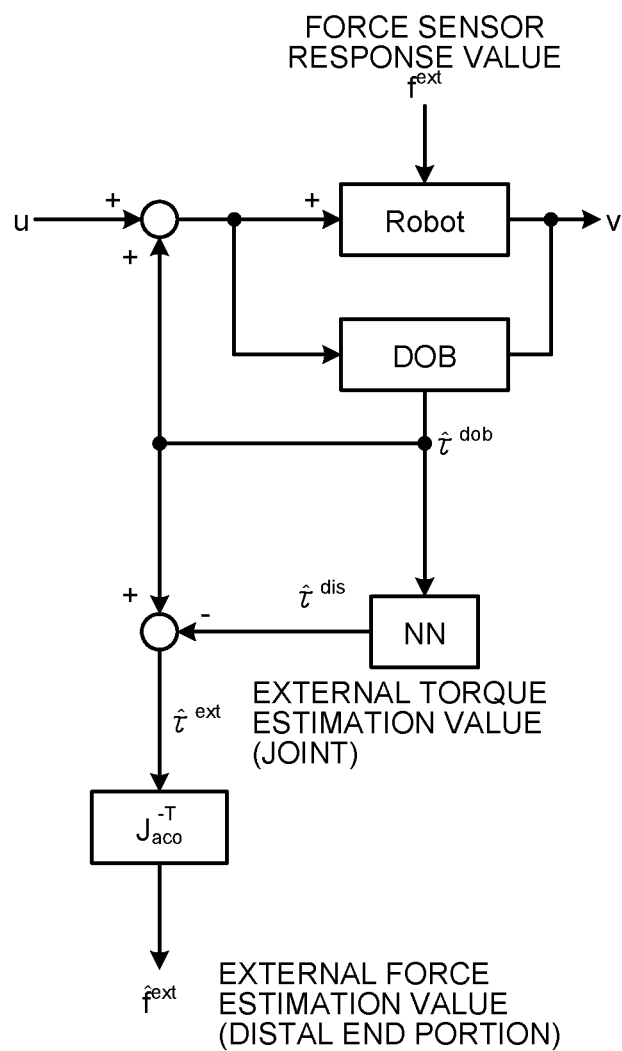
FIG. 14 is a diagram illustrating an example of information processing according to a first modification of the present disclosure.
Figure 15:
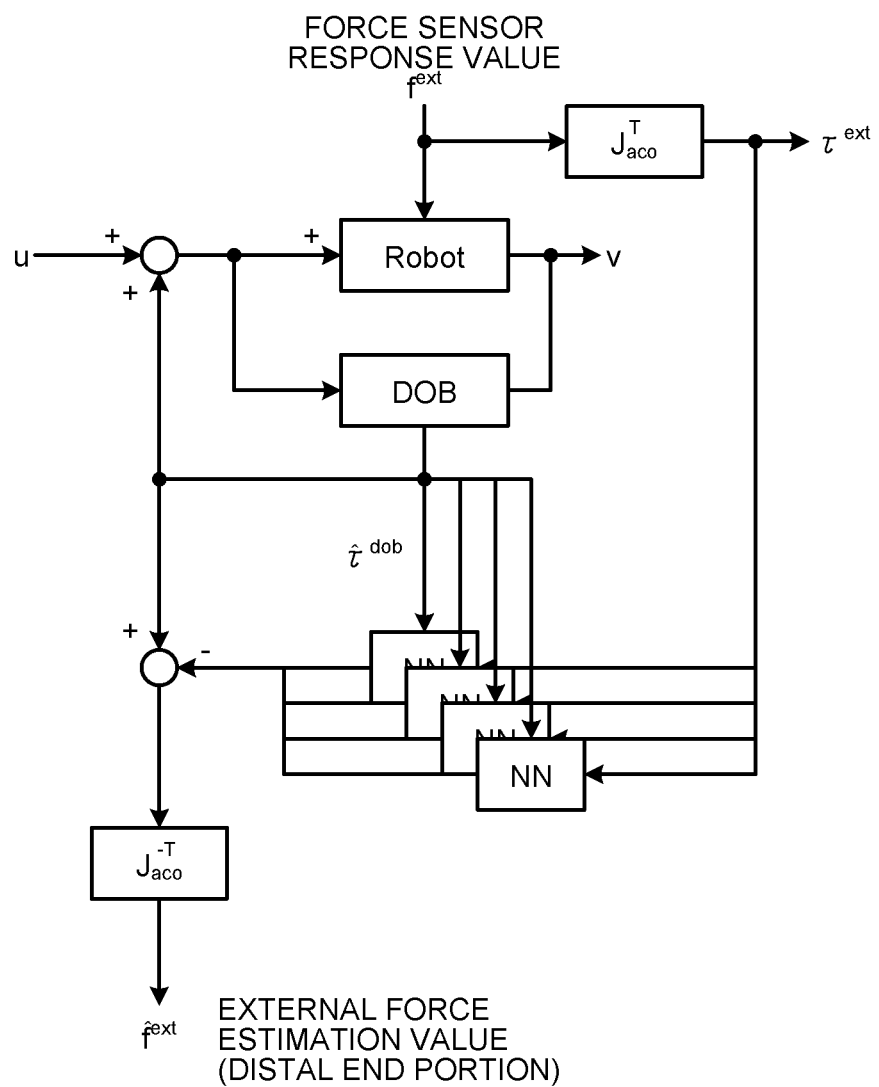
FIG. 15 is a diagram illustrating an example of information processing according to a second modification of the present disclosure.

That is, in the example illustrated in FIG. 14, the estimation unit 133 inputs the torque estimation value $\tau^{dob}$ ($\tau^{dob}$ added with a caret) of each joint portion calculated by the calculation unit 32 to the learned machine learning model M1, thereby estimating the disturbance torque estimation value $\tau_{dib}$ ($\tau^{dib}$ added with a caret) of each joint portion.

1-9-2. Second Modification of Embodiment

Next, an example of information processing according to the second modification of the present disclosure will be described with reference to FIG. 15. FIG. 15 is a diagram illustrating an example of information processing according to the second modification of the present disclosure. In the example illustrated in FIG. 15, the learning unit 135 learns a machine learning model for estimating a disturbance estimation value for each joint portion using an individual machine learning model for each joint portion. The estimation unit 133 estimates the external force estimation value using the machine learning model learned for each joint by the learning unit 135. As described above, the object to be driven includes one or more joint portions that rotate by driving of the motor, and the learning unit 135 learns an individual machine learning model for each joint portion. Furthermore, the estimation unit 133 estimates the external force estimation value for each joint portion using an individual machine learning model for each joint portion.

2. Other Embodiments

The information processing system 1 according to the above-described embodiment may be implemented in various different modes other than the above-described embodiment. Therefore, another embodiment of the information processing system 1 will be described below. The same parts as those in the embodiment are denoted by the same reference numerals, and the description thereof will be omitted.

2-1. Case where External Force Due to Contact Outside Force Sensor Acts

In the above-described embodiment, the example in which the external force acting on the distal end portion E1 of the arm portion and the disturbance acting on each joint portion of the arm portion act on the slave device 20 has been described. However, there is a case where the external force acts on the slave device 20 by contact with a location other than the location where the force sensor FS1 is installed. For example, there is a case where an external force acts on the slave device 20 when a person accidentally collides with the slave device 20 during surgery or a portion of the distal end portion E1 of the arm portion other than the portion where the force sensor FS1 is provided hits the opening of the patient.

An external force generated by contact with a place other than the place where the force sensor FS1 is installed cannot be detected by the force sensor FS1. Therefore, in the prior art, it is not possible to detect an external force generated by contact with a place other than the place where the force sensor FS1 is installed, and there is a possibility that dangerous operation is performed.

Therefore, the information processing system 1 according to the embodiment of the present disclosure uses the machine learning model M1 to estimate the external force estimation value $f^{ext}$ ($f^{ext}$ added with a caret) estimated to act on the distal end portion E1 of the arm portion on the basis of at least the torque estimation value $\tau^{dob}$ ($\tau^{dob}$ added with a caret) of each joint portion calculated by the disturbance observer.

That is, the information processing system 1 can estimate the external force estimation value $f^{ext}$ ($f^{ext}$ added with a caret) estimated to act on the distal end portion E1 of the arm portion on the basis of the torque estimation value $\tau^{dob}$ ($\tau^{dob}$ added with a caret) of each joint portion of the arm portion other than the distal end portion E1 of the arm portion by using the machine learning model M1. As a result, the information processing system 1 can estimate the external force estimation value $f^{ext}$ ($f^{ext}$ added with a caret) even if the information processing system 1 comes in contact with a place where the force sensor is not installed as well as a place where the force sensor is installed. Therefore, since the information processing system 1 can appropriately control the force of the robot apparatus, it is possible to prevent dangerous operation. For example, in the information processing system 1 by bilateral control according to the embodiment, even if the slave device 20 comes into contact with the outside of the force sensor FS1, the contact is transmitted to the operator on the master device 10 side, so that the risk to the patient can be reduced.

2-2. Application to Industrial Robot

In the above-described embodiment, an example in which the information processing system 1 is a master-slave information processing system by medical bilateral control has been described. The present invention can also be applied to an industrial robot. In a case where the information processing system 1 is applied to an industrial robot, it is possible to estimate an external force due to contact with a place where a force sensor is not installed, and thus, it is possible to reduce the risk at the time of cooperation with the industrial robot.

2-3. Application to Linear Motion Joint

In the above-described embodiment, an example in which each joint is a rotary joint that rotates by driving of the motor has been described. The present invention can also be applied to the object to be driven in which each joint is a linear motion joint. Here, the linear motion joint is a joint that slides so that only the position changes in one direction. Here, an example in which each joint of the arm portion includes the linear motion joint that slides by driving of the motor instead of the joint portion that rotates by driving of the motor will be described. Specifically, a linear motion joint portion of the arm portion slides by driving of the motor. The distal end portion of the arm portion is pushed out by sliding of the linear motion joint portion of the arm portion.

Specifically, the slave device 20 includes a motor, a joint portion that slides by driving of the motor, a force sensor that detects an external force acting on an arm portion with the joint portion, and a calculator that calculates a force estimation value that is an estimation value of a force acting on the joint portion on the basis of an input value input to the motor and an output value related to an output of the motor. Furthermore, the estimation unit 133 estimates an external force estimation value which is an estimation value for an external force that acts on an object to be driven (distal end portion of an arm portion) by performing a process based on a machine learning model with a force estimation value and an external force response value as an input, the force estimation value being an estimation value for a force that acts on the object to be driven (each joint portion), the external force response value being based on a value of an external force detected by a force sensor configured to detect the external force that acts on the object to be driven (distal end portion of the arm portion). Here, the external force response value is assumed to be an external force response value of each joint portion calculated on the basis of the value of the external force detected by the force sensor.

Specifically, the machine learning model includes a neural network computational model learned, on the basis of a force estimation value which is an estimation value for a force that acts on the object to be driven (each joint portion) and an external force response value (each joint portion) based on the value of the external force detected by the force sensor, so as to estimate an disturbance estimation value which is an estimation value regarding a disturbance that acts on the object to be driven (each joint portion), and the estimation unit 133 estimates the external force estimation value on the basis of a value obtained by subtracting the disturbance estimation value (each joint portion) estimated using the machine learning model from the force estimation value (each joint portion).

3. Effects According to Present Disclosure

As described above, the information processing apparatus (the information processing apparatus 100 in the embodiment) according to the present disclosure includes the estimation unit (the estimation unit 133 in the embodiment). The estimation unit estimates an external force estimation value which is an estimation value for an external force that acts on an object to be driven by performing a process based on a machine learning model with a force estimation value and an external force response value as an input, the force estimation value being an estimation value for a force that acts on the object to be driven, the external force response value being based on a value of an external force detected by a force sensor configured to detect the external force that acts on the object to be driven. Furthermore, the information processing apparatus (the slave device 20 in the embodiment) according to the present disclosure further includes the calculation unit (the calculation unit 23). The calculation unit calculates a force estimation value on the basis of an input value input to the motor and an output value related to an output of the motor.

As a result, the information processing apparatus according to the present disclosure can estimate the disturbance torque estimation value acting on each joint portion with higher accuracy than in the prior art, for example, using the torque estimation value calculated by the calculator and the external torque response value based on the external force detected by the force sensor (see FIG. 11). Furthermore, since the information processing apparatus can estimate the disturbance torque estimation value acting on each joint portion with high accuracy, the information processing apparatus can estimate the external torque estimation value of each joint portion with higher accuracy. Furthermore, since the information processing apparatus can estimate the external torque estimation value of each joint portion with higher accuracy, it is possible to estimate the external force estimation value estimated to have acted on the distal end portion of the arm portion with higher accuracy. Therefore, the information processing apparatus can appropriately control the operation of the robot apparatus.

Furthermore, the information processing apparatus can estimate the external force estimation value $f^{ext}$ ($f^{ext}$ added with a caret) estimated to act on the distal end portion E1 of the arm portion on the basis of the torque estimation value of each joint portion other than the place where the force sensor is installed, for example, by using the machine learning model. The external force estimation value can be estimated with high accuracy even if the information processing apparatus comes into contact with a place where the force sensor is not installed as well as a place where the force sensor is installed. Therefore, since the information processing apparatus can appropriately control the force of the robot apparatus, it is possible to prevent dangerous operation. For example, in the information processing system 1 by bilateral control according to the embodiment, even if the slave device 20 comes into contact with the outside of the force sensor FS1, the contact is transmitted to the operator on the master device 10 side, so that the risk to the patient can be reduced.

In addition, the machine learning model is a neural network computational model learned, on the basis of the force estimation value which is the estimation value for the force that acts on the object to be driven and the external force response value based on the value of the external force detected by the force sensor, so as to estimate a disturbance estimation value which is an estimation value regarding a disturbance that acts on the object to be driven, and the estimation unit estimates the external force estimation value on the basis of a value obtained by subtracting the disturbance estimation value estimated using the machine learning model from the force estimation value.

As a result, the information processing apparatus according to the present disclosure can estimate the external force estimation value with higher accuracy, for example, by subtracting the disturbance torque estimation value acting on each joint portion estimated with high accuracy from the torque estimation value.

Furthermore, the object to be driven includes one or more joint portions configured to be rotated by being driven by a motor, the force sensor detects an external force that acts on the object to be driven including the one or more joint portions, the force estimation value includes a torque estimation value which is an estimation value for a torque that acts on the one or more joint portions, the external force response value includes an external torque response value of the one or more joint portions, and the external torque response value is determined on the basis of the value of the external force, and the estimation unit estimates the external force estimation value by inputting the torque estimation value and the external torque response value to the machine learning model.

As a result, the information processing apparatus according to the present disclosure can estimate the disturbance torque estimation value acting on each joint portion with higher accuracy than in the prior art, using the torque estimation value calculated by the calculator and the external torque response value based on the external force detected by the force sensor (see FIG. 11). Furthermore, since the information processing apparatus can estimate the disturbance torque estimation value acting on each joint portion with high accuracy, the information processing apparatus can estimate the external torque estimation value of each joint portion with higher accuracy. Furthermore, since the information processing apparatus can estimate the external torque estimation value of each joint portion with higher accuracy, it is possible to estimate the external force estimation value estimated to have acted on the distal end portion of the arm portion with higher accuracy. Therefore, the information processing apparatus can appropriately control the operation of the robot apparatus.

Furthermore, the information processing apparatus can estimate the external force estimation value $f^{ext}$ ($f^{ext}$ added with a caret) estimated to act on the distal end portion E1 of the arm portion on the basis of the torque estimation value of each joint portion other than the place where the force sensor is installed by using the machine learning model. In addition, the information processing apparatus can estimate the external force estimation value with high accuracy even if the information processing apparatus comes in contact with a place where the force sensor is not installed as well as a place where the force sensor is installed. Therefore, since the information processing apparatus can appropriately control the force of the robot apparatus, it is possible to prevent dangerous operation. For example, in the information processing system 1 by bilateral control according to the embodiment, even if the slave device 20 comes into contact with the outside of the force sensor FS1, the contact is transmitted to the operator on the master device 10 side, so that the risk to the patient can be reduced.

Furthermore, the machine learning model includes a neural network computational model learned, on the basis of a torque estimation value which is an estimation value for a force that acts on the object to be driven and an external torque response value based on the value of the external force detected by the force sensor, so as to estimate a disturbance torque estimation value which is an estimation value regarding a disturbance that acts on the object to be driven, and the estimation unit estimates the external force estimation value on the basis of a value obtained by subtracting the disturbance torque estimation value estimated using the machine learning model from the torque estimation value.

As a result, the information processing apparatus according to the present disclosure can estimate the external force estimation value with higher accuracy by subtracting the disturbance torque estimation value acting on each joint portion estimated with high accuracy from the torque estimation value.

Furthermore, the estimation unit estimates the external force estimation value by performing coordinate transformation, from a joint space value to an operation space value, on the value obtained by subtracting the disturbance torque estimation value estimated using the machine learning model from the torque estimation value.

As a result, the information processing apparatus according to the present disclosure can estimate the external force estimation value with high accuracy even if the information processing apparatus comes into contact with a place where the force sensor is not installed as well as a place where the force sensor is installed.

Furthermore, the information processing apparatus (the information processing apparatus 100 in the embodiment) according to the present disclosure further includes the learning unit (the learning unit 135). The learning unit learns the machine learning model that estimates the disturbance estimation value on the basis of the learning data including the force estimation value that is the estimation value of the force acting on the object to be driven and the external force response value based on the value of the external force detected by the force sensor. The estimation unit estimates the external force estimation value using the machine learning model learned by the learning unit. In addition, the object to be driven includes one or more joint portions configured to be rotated by being driven by a motor, the force sensor detects an external force that acts on the object to be driven including the one or more joint portions, the force estimation value includes a torque estimation value which is an estimation value for a torque that acts on the one or more joint portions, the external force response value includes an external torque response value of the one or more joint portions, and the external torque response value is determined on the basis of the value of the external force, the disturbance estimation value includes a disturbance torque estimation value which is an estimation value regarding a disturbance that acts on the one or more joint portions, the learning unit learns the machine learning model configured to estimate the disturbance torque estimation value for each of the one or more joint portions on the basis of learning data including the torque estimation value for the one or more joint portions and the external torque response value of the one or more joint portions, and the estimation unit estimates the external force estimation value using the machine learning model learnt by the learning unit.

As a result, the information processing apparatus according to the present disclosure can estimate the external force estimation value with higher accuracy than in the prior art (see FIG. 11).

In addition, the learning unit learns the machine learning model on the basis of the learning data including the combination of the first learning data in the load state in which the force sensor is in contact with the contact target and the second learning data in the no-load state in which the force sensor is not in contact with the contact target.

As a result, the information processing apparatus according to the present disclosure can estimate the external force estimation value with high accuracy even if the information processing apparatus comes into contact with a place where the force sensor is not installed as well as a place where the force sensor is installed.

In addition, the object to be driven includes one or more joint portions that rotate by driving of the motor. The learning unit learns an individual machine learning model for each joint portion. The estimation unit estimates the external force estimation value for each joint portion using an individual machine learning model for each joint portion.

As a result, the information processing apparatus according to the present disclosure can estimate the external force estimation value using the machine learning model learned for each joint.

In addition, the force sensor detects an external force acting on a part of the object to be driven.

As a result, the information processing apparatus according to the present disclosure can estimate the external force estimation value even if the information processing apparatus comes into contact with a place where the force sensor is not installed as well as a place where the force sensor is installed.

In addition, the estimation unit estimates the external force estimation value using a machine learning model having a function of long short-term memory (LSTM).

As a result, the information processing apparatus according to the present disclosure can cause the machine learning model to learn in consideration of the time series of the learning data.

In addition, the object to be driven is a multi-link structure formed by coupling a plurality of links to one another with a joint portion.

As a result, the information processing apparatus according to the present disclosure can estimate the external force estimation value estimated to have acted on the multi-link structure with higher accuracy. Therefore, the information processing apparatus can appropriately control the operation of the robot apparatus.

4. Hardware Configuration

Figure 16:
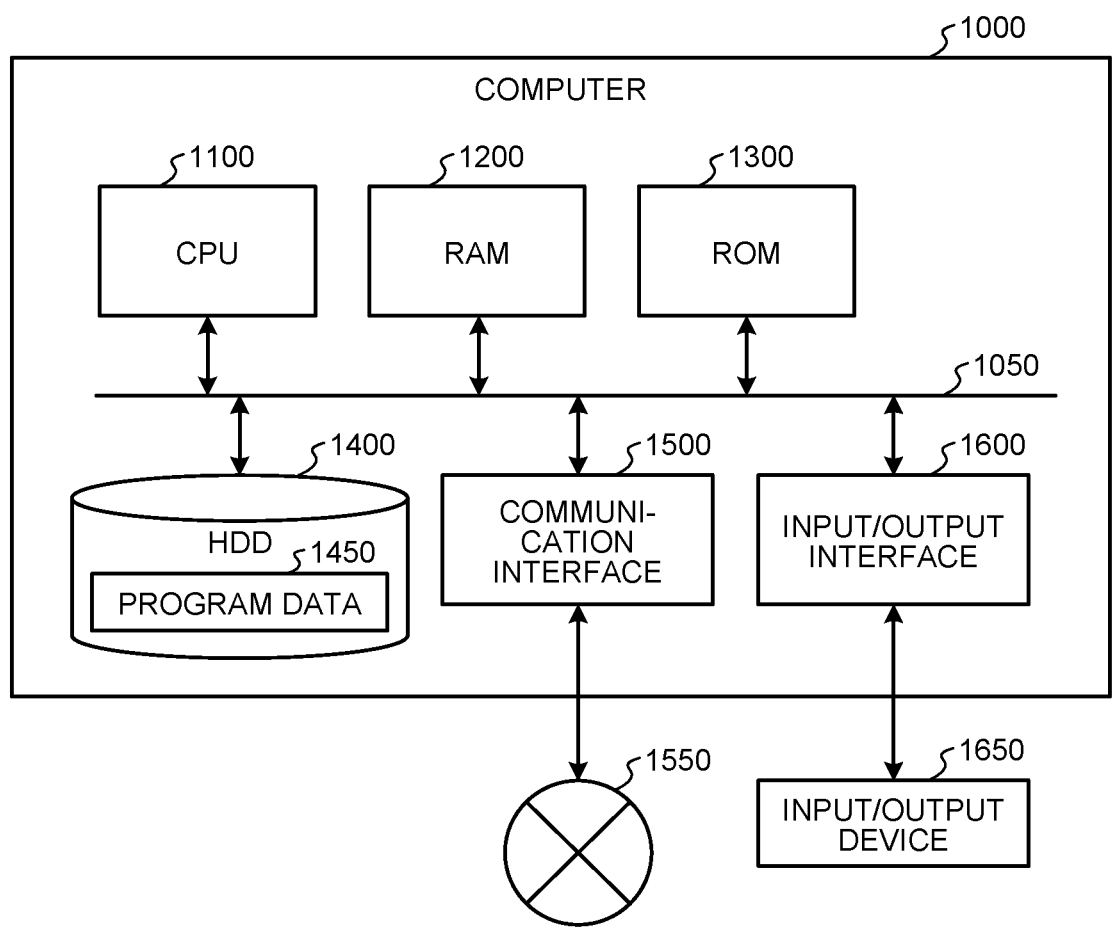
FIG. 16 is a hardware configuration diagram illustrating an example of a computer that implements functions of the information processing apparatus.

The information device such as the information processing apparatus 100 according to the above-described embodiments and modifications is implemented by a computer 1000 having a configuration as illustrated in FIG. 16, for example. FIG. 16 is a hardware configuration diagram illustrating an example of the computer 1000 that implements the functions of the information processing apparatus such as the information processing apparatus 100. Hereinafter, the information processing apparatus 100 according to the embodiment will be described as an example. The computer 1000 includes a CPU 1100, a RAM 1200, a read only memory (ROM) 1300, a hard disk drive (HDD) 1400, a communication interface 1500, and an input/output interface 1600. Each unit of the computer 1000 is connected by a bus 1050.

The CPU 1100 operates on the basis of a program stored in the ROM 1300 or the HDD 1400, and controls each unit. For example, the CPU 1100 decompresses a program stored in the ROM 1300 or the HDD 1400 in the RAM 1200, and executes processing corresponding to various programs.

The ROM 1300 stores a boot program such as a basic input output system (BIOS) executed by the CPU 1100 when the computer 1000 is started, a program depending on hardware of the computer 1000, and the like.

The HDD 1400 is a computer-readable recording medium that non-transiently records a program executed by the CPU 1100, data used by the program, and the like. Specifically, the HDD 1400 is a recording medium that records an information processing program according to the present disclosure, which is an example of the program data 1450.

The communication interface 1500 is an interface for the computer 1000 to connect to an external network 1550 (for example, the Internet). For example, the CPU 1100 receives data from another device or transmits data generated by the CPU 1100 to another device via the communication interface 1500.

The input/output interface 1600 is an interface for connecting the input/output device 1650 and the computer 1000. For example, the CPU 1100 receives data from an input device such as a keyboard and a mouse via the input/output interface 1600. In addition, the CPU 1100 transmits data to an output device such as a display, a speaker, or a printer via the input/output interface 1600. Furthermore, the input/output interface 1600 may function as a media interface that reads a program or the like recorded in a predetermined recording medium (medium). The medium is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, in a case where the computer 1000 functions as the information processing apparatus 100 according to the embodiment, the CPU 1100 of the computer 1000 implements the functions of the control unit 130 and the like by executing the information processing program loaded on the RAM 1200. In addition, the HDD 1400 stores an information processing program according to the present disclosure and data in the storage unit 120. Note that the CPU 1100 reads the program data 1450 from the HDD 1400 and executes the program data, but as another example, these programs may be acquired from another device via the external network 1550.

Note that the present technology can also have the following configurations.

(1)

An information processing apparatus comprising:
an estimation unit configured to estimate an external force estimation value which is an estimation value for an external force that acts on an object to be driven by performing a process based on a machine learning model with a force estimation value and an external force response value as an input, the force estimation value being an estimation value for a force that acts on the object to be driven, the external force response value being based on a value of an external force detected by a force sensor configured to detect the external force that acts on the object to be driven.

(2)

The information processing apparatus according to (1), further comprising
a calculation unit configured to calculate the force estimation value on the basis of an input value which is input to a motor configured to move the object to be driven and an output value regarding an output of the motor.

(3)

The information processing apparatus according to (1) or (2),
wherein the machine learning model includes a neural network computational model learned, on the basis of the force estimation value which is the estimation value for the force that acts on the object to be driven and the external force response value based on the value of the external force detected by the force sensor, so as to estimate a disturbance estimation value which is an estimation value regarding a disturbance that acts on the object to be driven, and
the estimation unit estimates the external force estimation value on the basis of a value obtained by subtracting the disturbance estimation value estimated using the machine learning model from the force estimation value.

(4)

The information processing apparatus according to (1) or (2), wherein the object to be driven includes one or more joint portions configured to be rotated by being driven by a motor, the force sensor detects an external force that acts on the object to be driven including the one or more joint portions, the force estimation value includes a torque estimation value which is an estimation value for a torque that acts on the one or more joint portions, the external force response value includes an external torque response value of the one or more joint portions, and the external torque response value is determined on the basis of the value of the external force, and the estimation unit estimates the external force estimation value by inputting the torque estimation value and the external torque response value to the machine learning model.

(5)

The information processing apparatus according to (4), wherein the machine learning model includes a neural network computational model learned, on the basis of a torque estimation value which is an estimation value for a force that acts on the object to be driven and an external torque response value based on the value of the external force detected by the force sensor, so as to estimate a disturbance torque estimation value which is an estimation value regarding a disturbance that acts on the object to be driven, and the estimation unit estimates the external force estimation value on the basis of a value obtained by subtracting the disturbance torque estimation value estimated using the machine learning model from the torque estimation value.

(6)

The information processing apparatus according to (5), wherein the estimation unit estimates the external force estimation value by performing coordinate transformation, from a joint space value to an operation space value, on the value obtained by subtracting the disturbance torque estimation value estimated using the machine learning model from the torque estimation value.

(7)

The information processing apparatus according to any of (1) to (3), further comprising a learning unit configured to learn the machine learning model configured to estimate the disturbance estimation value which is the estimation value regarding the disturbance that acts on the object to be driven on the basis of learning data including the force estimation value which is the estimation value for the force that acts on the object to be driven and the external force response value based on the value of the external force detected by the force sensor, wherein the estimation unit estimates the external force estimation value using the machine learning model learnt by the learning unit.

(8)

The information processing apparatus according to (7), wherein the object to be driven includes one or more joint portions configured to be rotated by being driven by a motor, the force sensor detects an external force that acts on the object to be driven including the one or more joint portions, the force estimation value includes a torque estimation value which is an estimation value for a torque that acts on the one or more joint portions, the external force response value includes an external torque response value of the one or more joint portions, and the external torque response value is determined on the basis of the value of the external force, the disturbance estimation value includes a disturbance torque estimation value which is an estimation value regarding a disturbance that acts on the one or more joint portions, the learning unit learns the machine learning model configured to estimate the disturbance torque estimation value for each of the one or more joint portions on the basis of learning data including the torque estimation value for the one or more joint portions and the external torque response value of the one or more joint portions, and the estimation unit estimates the external force estimation value using the machine learning model learnt by the learning unit.

(9)

The information processing apparatus according to (7) or (8), wherein the learning unit learns the machine learning model on the basis of the learning data including a combination of first learning data in a load state in which the force sensor is in contact with a contact target and second learning data in a no-load state in which the force sensor is not in contact with the contact target.

(10)

The information processing apparatus according to any of (7) to (9), wherein the learning unit learns a plurality of the machine learning models each of which is individualized for a different one of the one or more joint portions, and the estimation unit estimates the external force estimation value for each of the one or more joint portions using the plurality of machine learning models each of which is individualized for the different one of the one or more joint portions.

(11)

The information processing apparatus according to any of (1) to (10), wherein the force sensor detects an external force that acts on a part of the object to be driven.

(12)

The information processing apparatus according to any of (1) to (11), wherein the estimation unit estimates the external force estimation value using the machine learning model having a function of Long Short-Term Memory (LSTM).

(13)

The information processing apparatus according to any of (1) to (12), wherein the object to be driven includes a multi-link structure formed by coupling a plurality of links to one another with a joint portion.

(14)

An information processing system, comprising:

a robot apparatus; and an information processing apparatus configured to remotely operate the robot apparatus, wherein the robot apparatus includes:

a motor;

an object to be driven configured to be moved by being driven by the motor; and a force sensor configured to detect an external force that acts on the object to be driven, and the information processing apparatus includes an estimation unit configured to estimate an external force estimation value which is an estimation value for the external force that acts on the object to be driven by performing a process based on a machine learning model with a force estimation value and an external force response value as an input, the force estimation value being an estimation value for a force that acts on the object to be driven, the external force response value being based on a value of the external force detected by the force sensor.

(15)

An information processing method for performing a process, the process comprising:

estimating an external force estimation value which is an estimation value for an external force that acts on an object to be driven by performing a process based on a machine learning model with a force estimation value and an external force response value as an input, the force estimation value being an estimation value for a force that acts on the object to be driven, the external force response value being based on a value of an external force detected by a force sensor configured to detect the external force that acts on the object to be driven.

REFERENCE SIGNS LIST

1 Information Processing System
10 Master Device
20 Slave Device
21 Drive Unit
22 Detection Unit
23 Calculation Unit
24 Communication Unit
100 Information Processing Apparatus
110 Communication Unit
120 Storage Unit
121 Model Information Storage Unit
130 Control Unit
131 Acquisition Unit
132 Calculation Unit
133 Estimation Unit
134 Operation Control Unit
135 Learning Unit

The invention claimed is:

1. An information processing apparatus, comprising:

processing circuitry configured to estimate an external force estimation value which is an estimation value for an external force that acts on an object to be driven by execution of a process based on a machine learning model with a force estimation value and an external force response value as an input, the force estimation value being an estimation value for a force that acts on the object to be driven, the external force response value being based on a value of an external force detected by a force sensor configured to detect the external force that acts on the object to be driven.

2. The information processing apparatus according to claim 1, wherein the processing circuitry is further configured to:

calculate the force estimation value based on an input value which is input to a motor configured to move the object to be driven; and calculate an output value regarding an output of the motor.

3. The information processing apparatus according to claim 1, wherein the machine learning model includes a neural network computational model learned, based on the force estimation value which is the estimation value for the force that acts on the object to be driven and the external force response value based on the value of the external force detected by the force sensor, so as to estimate a disturbance estimation value which is an estimation value regarding a disturbance that acts on the object to be driven, and the processing circuitry is further configured to estimate the external force estimation value based on a value obtained by subtraction of the disturbance estimation value estimated using the machine learning model from the force estimation value.

4. The information processing apparatus according to claim 1, wherein the object to be driven includes one or more joint portions configured to be rotated by being driven by a motor, the force sensor detects an external force that acts on the object to be driven including the one or more joint portions, the force estimation value includes a torque estimation value which is an estimation value for a torque that acts on the one or more joint portions, the external force response value includes an external torque response value of the one or more joint portions, and the external torque response value is determined based on the value of the external force, and the processing circuitry is further configured to estimate the external force estimation value by input of the torque estimation value and the external torque response value to the machine learning model.

5. The information processing apparatus according to claim 4, wherein the machine learning model includes a neural network computational model learned, based on a torque estimation value which is an estimation value for a force that acts on the object to be driven and an external torque response value based on the value of the external force detected by the force sensor, so as to estimate a disturbance torque estimation value which is an estimation value regarding a disturbance that acts on the object to be driven, and the processing circuitry is further configured to estimate the external force estimation value based on a value obtained by subtraction of the disturbance torque estimation value estimated using the machine learning model from the torque estimation value.

6. The information processing apparatus according to claim 5, wherein the processing circuitry is further configured to estimate the external force estimation value by performing coordinate transformation, from a joint space value to an operation space value, on the value obtained by subtraction of the disturbance torque estimation value estimated using the machine learning model from the torque estimation value.

7. The information processing apparatus according to claim 3, the processing circuitry is further configured to learn the machine learning model configured to estimate the disturbance estimation value which is the estimation value regarding the disturbance that acts on the object to be driven based on learning data including the force estimation value which is the estimation value for the force that acts on the object to be driven and the external force response value based on the value of the external force detected by the force sensor, wherein the processing circuitry is further configured to estimate the external force estimation value using the machine learning model.

8. The information processing apparatus according to claim 7, wherein the object to be driven includes one or more joint portions configured to be rotated by being driven by a motor, the force sensor detects an external force that acts on the object to be driven including the one or more joint portions, the force estimation value includes a torque estimation value which is an estimation value for a torque that acts on the one or more joint portions, the external force response value includes an external torque response value of the one or more joint portions, and the external torque response value is determined based on the value of the external force, the disturbance estimation value includes a disturbance torque estimation value which is an estimation value regarding a disturbance that acts on the one or more joint portions, and the processing circuitry is further configured to:

learn the machine learning model configured to estimate the disturbance torque estimation value for each of the one or more joint portions based on learning data including the torque estimation value for the one or more joint portions and the external torque response value of the one or more joint portions; and estimate the external force estimation value using the machine learning model.

9. The information processing apparatus according to claim 7, wherein the processing circuitry is further configured to learn the machine learning model based on the learning data including a combination of first learning data in a load state in which the force sensor is in contact with a contact target and second learning data in a no-load state in which the force sensor is not in contact with the contact target.

10. The information processing apparatus according to claim 7, wherein the processing circuitry is further configured to:

learn a plurality of machine learning models each of which is individualized for a different one of one or more joint portions; and estimate the external force estimation value for each of the one or more joint portions using the plurality of machine learning models each of which is individualized for the different one of the one or more joint portions.

11. The information processing apparatus according to claim 1, wherein the force sensor is further configured to detect an external force that acts on a part of the object to be driven.

12. The information processing apparatus according to claim 1, wherein the processing circuitry is further configured to estimate the external force estimation value using the machine learning model having a function of Long Short-Term Memory (LSTM).

13. The information processing apparatus according to claim 1, wherein the object to be driven includes a multi-link structure formed by coupling a plurality of links with a joint portion.

14. An information processing system, comprising:

a robot apparatus; and an information processing apparatus configured to remotely operate the robot apparatus, wherein the robot apparatus includes:

a motor;

an object to be driven configured to be moved by being driven by the motor; and a force sensor configured to detect an external force that acts on the object to be driven, and the information processing apparatus includes processing circuitry configured to estimate an external force estimation value which is an estimation value for the external force that acts on the object to be driven by execution of a process based on a machine learning model with a force estimation value and an external force response value as an input, the force estimation value being an estimation value for a force that acts on the object to be driven, the external force response value being based on a value of the external force detected by the force sensor.

15. An information processing method, comprising:

estimating an external force estimation value which is an estimation value for an external force that acts on an object to be driven by performing a process based on a machine learning model with a force estimation value and an external force response value as an input, the force estimation value being an estimation value for a force that acts on the object to be driven, the external force response value being based on a value of an external force detected by a force sensor configured to detect the external force that acts on the object to be driven.

* * * * *